United States Patent
Kuwabara et al.

(10) Patent No.: US 9,060,738 B2
(45) Date of Patent: *Jun. 23, 2015

(54) RADIOGRAPHIC SYSTEM, AUTOMATIC EXPOSURE CONTROL METHOD OF RADIOGRAPHIC SYSTEM, AND RADIOLOGICAL IMAGE DETECTOR

(75) Inventors: Takeshi Kuwabara, Kanagawa (JP); Takeshi Kamiya, Kanagawa (JP); Yusuke Kitagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 329 days.

This patent is subject to a terminal disclaimer.

(21) Appl. No.: 13/603,099

(22) Filed: Sep. 4, 2012

(65) Prior Publication Data

US 2013/0058457 A1 Mar. 7, 2013

(30) Foreign Application Priority Data

Sep. 5, 2011 (JP) .................................. 2011-193187

(51) Int. Cl.
*A61B 6/06* (2006.01)
*A61B 6/00* (2006.01)

(52) U.S. Cl.
CPC ............... *A61B 6/542* (2013.01); *A61B 6/4494* (2013.01); *A61B 6/4233* (2013.01); *A61B 6/548* (2013.01)

(58) Field of Classification Search
CPC ........ A61B 6/542; A61B 6/544; A61B 6/545; A61B 6/56; A61B 6/566; A61B 6/58; A61B 6/585; A61B 6/4283
USPC .......... 378/51, 62, 96, 97, 162, 165, 114, 115
See application file for complete search history.

(56) References Cited

U.S. PATENT DOCUMENTS

| | | | |
|---|---|---|---|
| 2004/0096035 A1* | 5/2004 | Yamazaki et al. | 378/97 |
| 2005/0279943 A1* | 12/2005 | Kobayashi et al. | 250/370.09 |
| 2011/0180717 A1* | 7/2011 | Okada | 250/370.08 |
| 2013/0058454 A1* | 3/2013 | Kuwabara et al. | 378/62 |

FOREIGN PATENT DOCUMENTS

| | | | |
|---|---|---|---|
| EP | 1 420 618 A2 | 5/2004 | |
| EP | 1 440 660 A2 | 7/2004 | |
| JP | 07-201490 A | 8/1995 | |
| JP | 2003-302716 A | 10/2003 | |

(Continued)

OTHER PUBLICATIONS

Communication, dated Dec. 18, 2012, issued in corresponding EP Application No. 12182762.0, 8 pages.

*Primary Examiner* — Robert Kim
*Assistant Examiner* — David E Smith
(74) *Attorney, Agent, or Firm* — Sughrue Mion, PLLC

(57) ABSTRACT

A storage and search unit of a console acquires a source ID of an X-ray source and searches for and extracts a type corresponding to the acquired source ID from source information of a storage device. In the case of an installation convenience preference type in which convenience in connection between a source controller and an electronic cassette is preferred, a detection signal from a detection pixel of an FPD of the electronic cassette is output from a detection signal I/F of the electronic cassette to a detection signal I/F of the source controller. In the case of an installation convenience non-preference type, an irradiation stop signal based on the comparison result of the integrated value of the detection signal from the detection pixel with an irradiation-stop threshold is output from an irradiation signal I/F of the electronic cassette to an irradiation signal I/F of the source controller.

21 Claims, 25 Drawing Sheets

(56) References Cited

FOREIGN PATENT DOCUMENTS

| WO | 2005098535 A1 | 10/2005 | | |
| WO | WO 2005098535 A1 | * 10/2005 | ............. | G03B 42/04 |
| WO | 2006046206 A1 | 5/2006 | | |
| WO | WO 2006046206 A1 | * 5/2006 | ............... | A61B 6/00 |

* cited by examiner

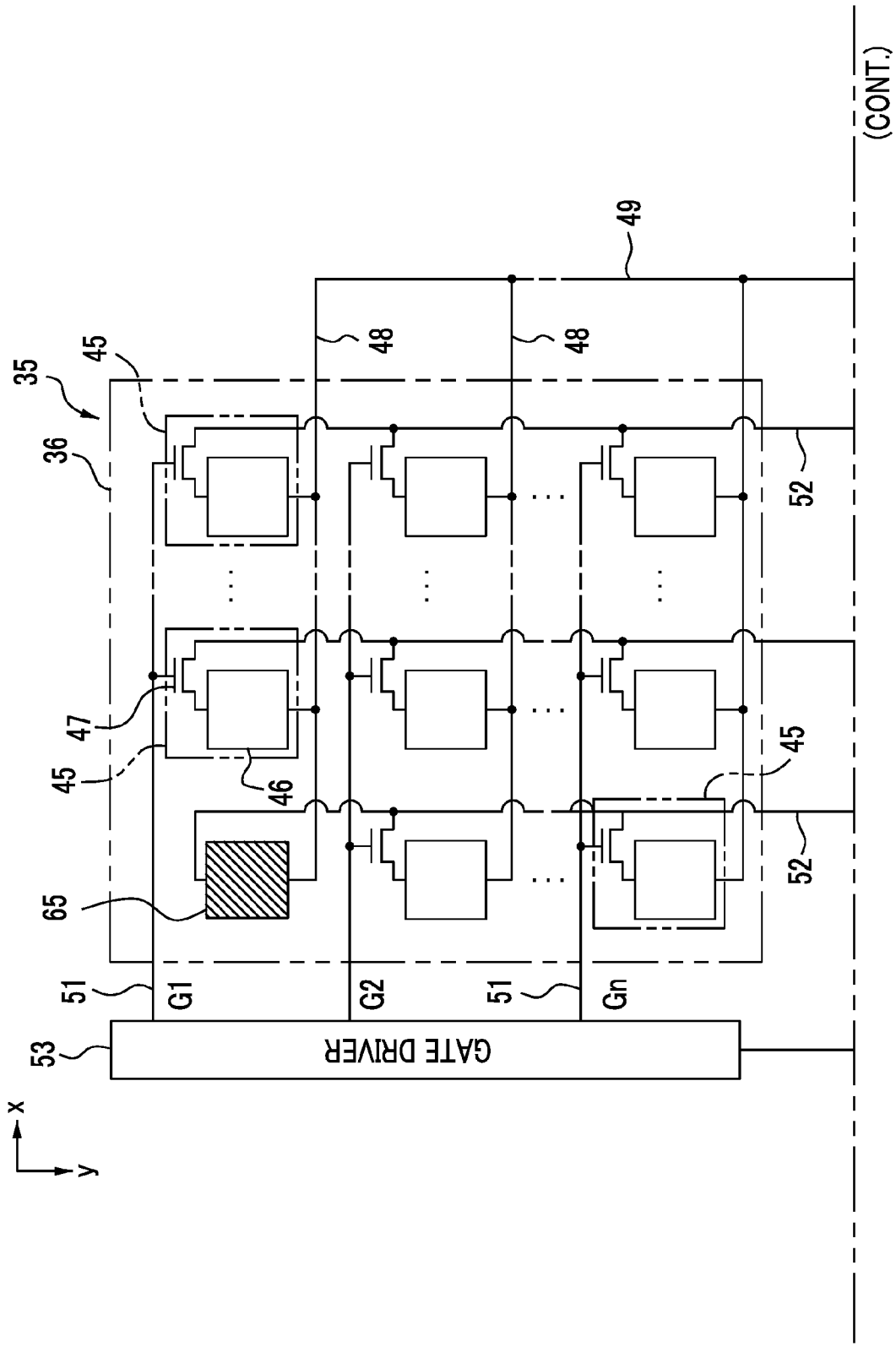

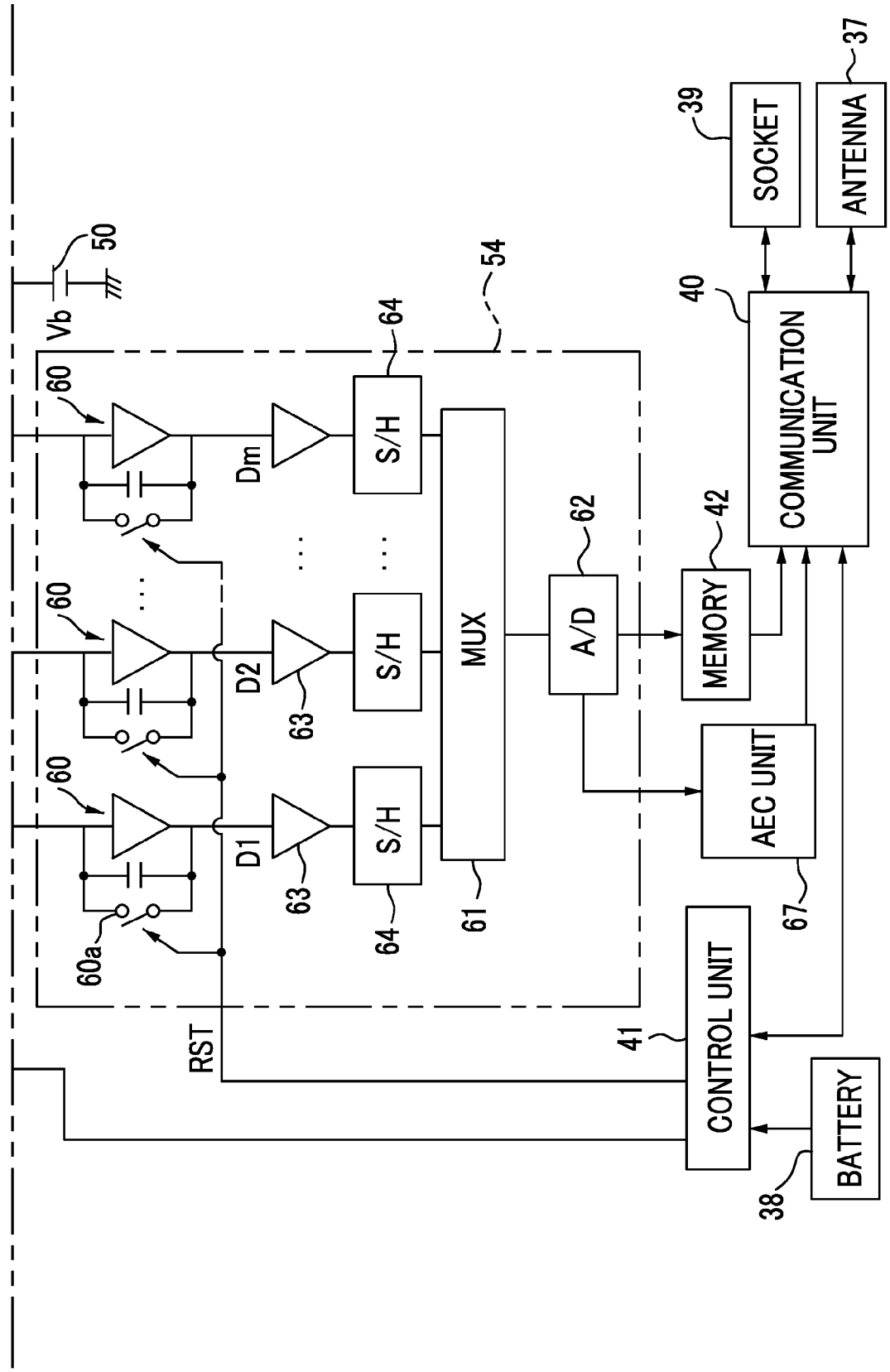

FIG. 6

| No. | RADIOGRAPHED SITE | TUBE CURRENT (kV) | S VALUE | ... |
|---|---|---|---|---|
| 1 | CHEST PA | 120 | S1 | |
| 2 | CHEST AP | | S2 | |
| 3 | CHEST FRONT | | S3 | ... |
| ⋮ | ⋮ | | ⋮ | |
| 48 | HEAD PA | 50 | S48 | |
| 49 | HEAD AP | | S49 | |
| 50 | HEAD SIDE | | S50 | |
| ⋮ | ⋮ | | ⋮ | |

FIG. 9

| SOURCE ID | REGIONAL TYPE | | RADIOGR-APHING CONDITION | AEC SPECIFICATION | | CORRECTION INFORMATION |
|---|---|---|---|---|---|---|
| | REGION | TYPE | | INTEGR-ATION CIRCUIT | DETECTION FIELD POSITION | |
| 001 | DOMES-TIC 1 | INSTALL-ATION CONVENI-ENCE NON-PREFE-RENCE | No. 1 120kV 1mAs DETECTION FILED a, b··· | ABSENT | a:(x1, y1) ~(x2, y2) ... | (graph: NEW AEC DETECTION SIGNAL vs OLD AEC DETECTION SIGNAL; TUBE VOLTAGE A, TUBE VOLTAGE B, TUBE VOLTAGE C, TUBE VOLTAGE D) |
| | DOMES-TIC 2 | INSTALL-ATION CONVENI-ENCE NON-PREFE-RENCE | ... | | ... | ... |
| | NORTH AMERICA 1 | INSTALL-ATION CONVENI-ENCE NON-PREFE-RENCE | | | | |
| | NORTH AMERICA 2 | INSTALL-ATION CONVENI-ENCE PREFE-RENCE | | | | |

| | | No. 1 115kV<br>1.5mAs<br>DETECTION<br>FILED<br>a TO e··· | a:(x3, y3)<br>~ (x4, y4)<br>··· |
|---|---|---|---|
| EUROPE 1 | INSTALL-<br>ATION-<br>CONVENI-<br>ENCE<br>NON-<br>PREFE-<br>RENCE | | |
| EUROPE 2 | INSTALL-<br>ATION-<br>CONVENI-<br>ENCE<br>PREFE-<br>RENCE | | |
| ASIA 1 | INSTALL-<br>ATION-<br>CONVENI-<br>ENCE<br>PREFE-<br>RENCE | | |
| ASIA 2 | | | |
| DOMES-<br>TIC 1 | INSTALL-<br>ATION-<br>CONVENI-<br>ENCE<br>NON-<br>PREFE-<br>RENCE | | |
| DOMES-<br>TIC 2 | | | |

(CONT.)

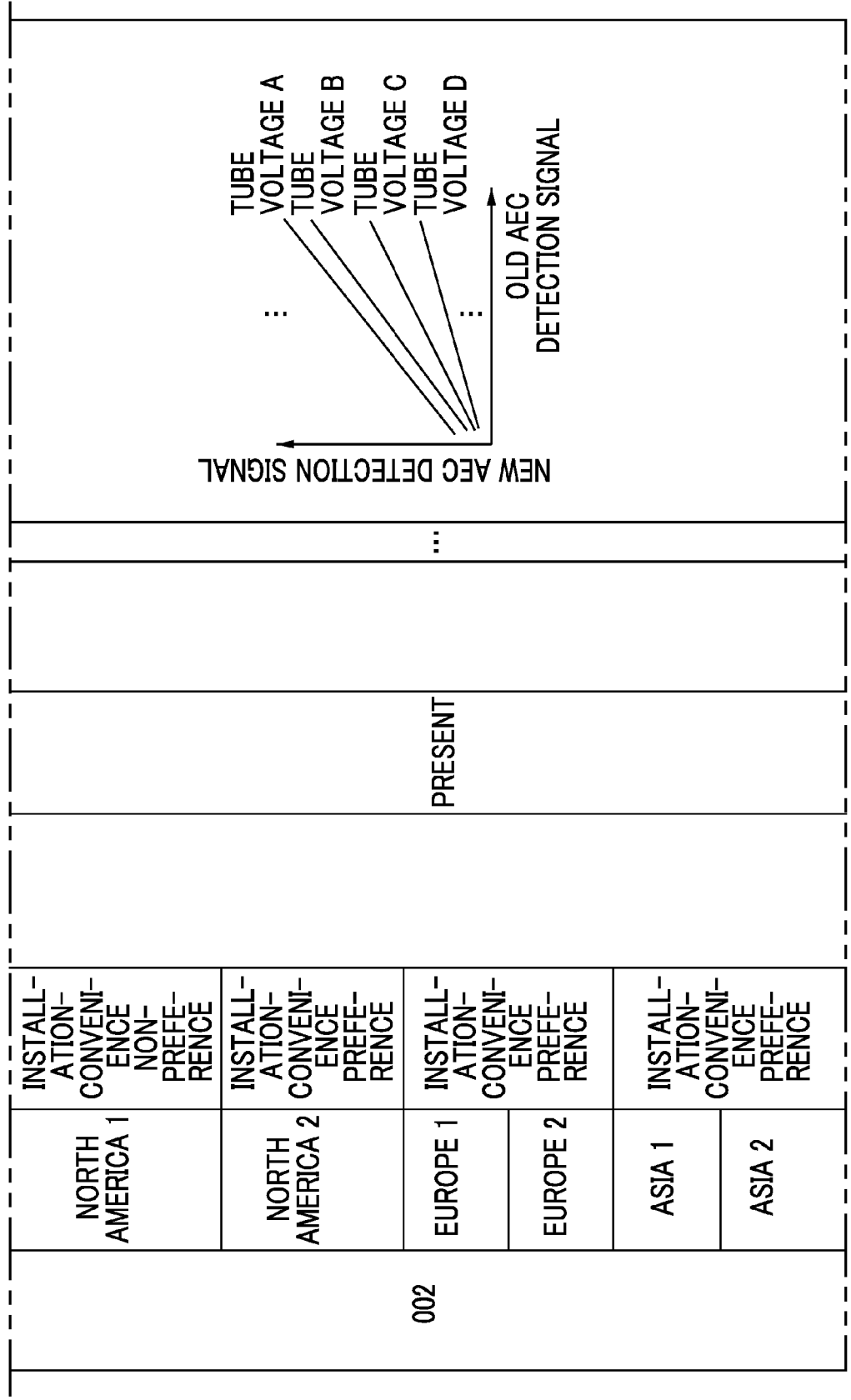

FIG. 10

| REGIONAL TYPE | INSTALLATION CONVENIENCE PREFERENCE | INSTALLATION CONVENIENCE NON-PREFERENCE |
|---|---|---|
| INSTALLATION CONVENIENCE | ◯ | △ |
| IMAGE QUALITY | △ | ◯ |
| OUTPUT DESTINATION | DETECTION SIGNAL I/F | IRRADIATION SIGNAL I/F |
| OUTPUT FORMAT | DETECTION SIGNAL | IRRADIATION PROHIBITION SIGNAL |
| CORRECTION OF DETECTED VALUE | NECESSARY | NECESSARY |
| REPLACEMENT OF THRESHOLD | UNNECESSARY | NECESSARY |
| DETERMINATION OF IRRADIATION STOP | X-RAY SOURCE SIDE | ELECTRONIC CASSETTE SIDE |

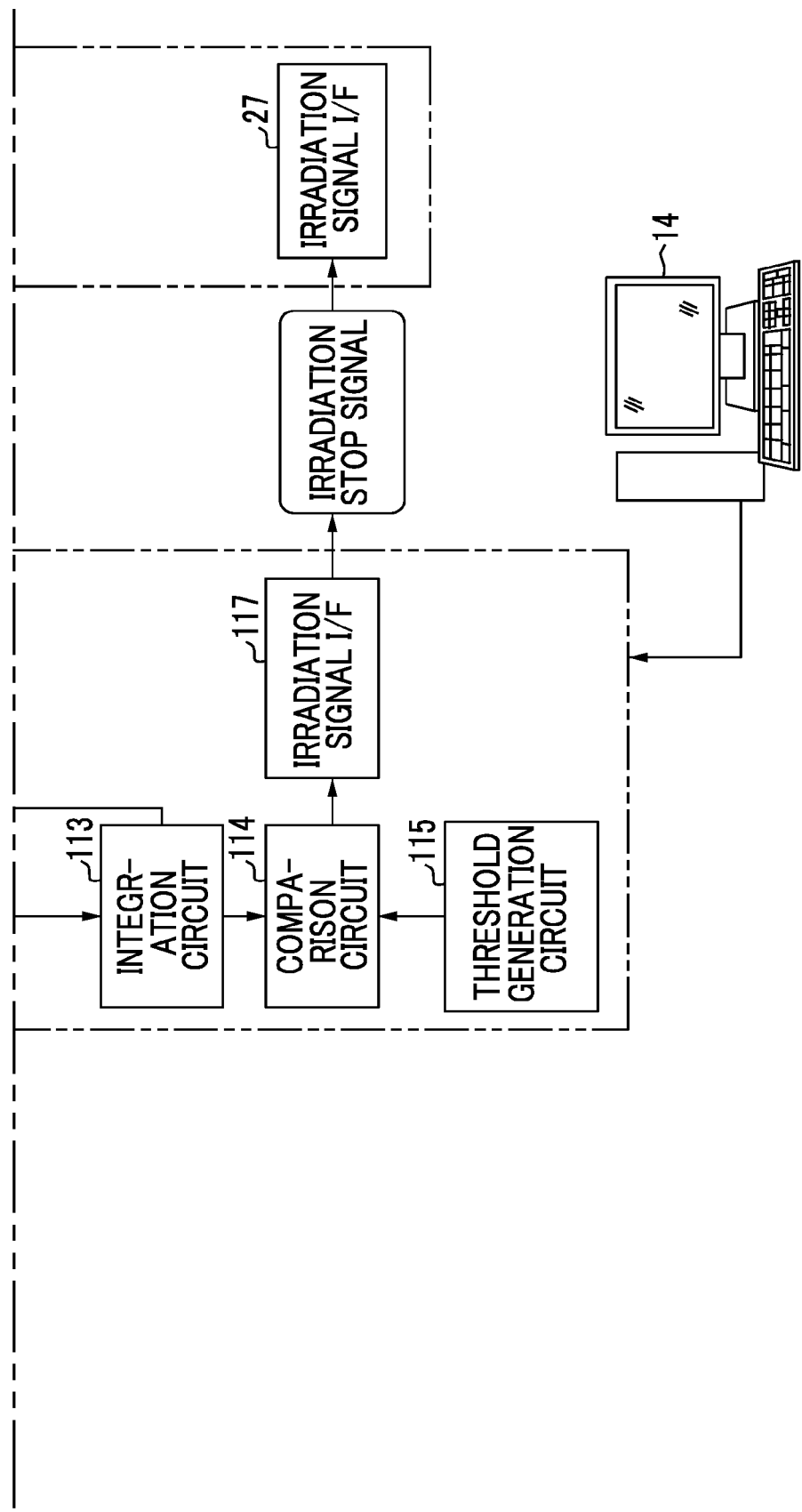

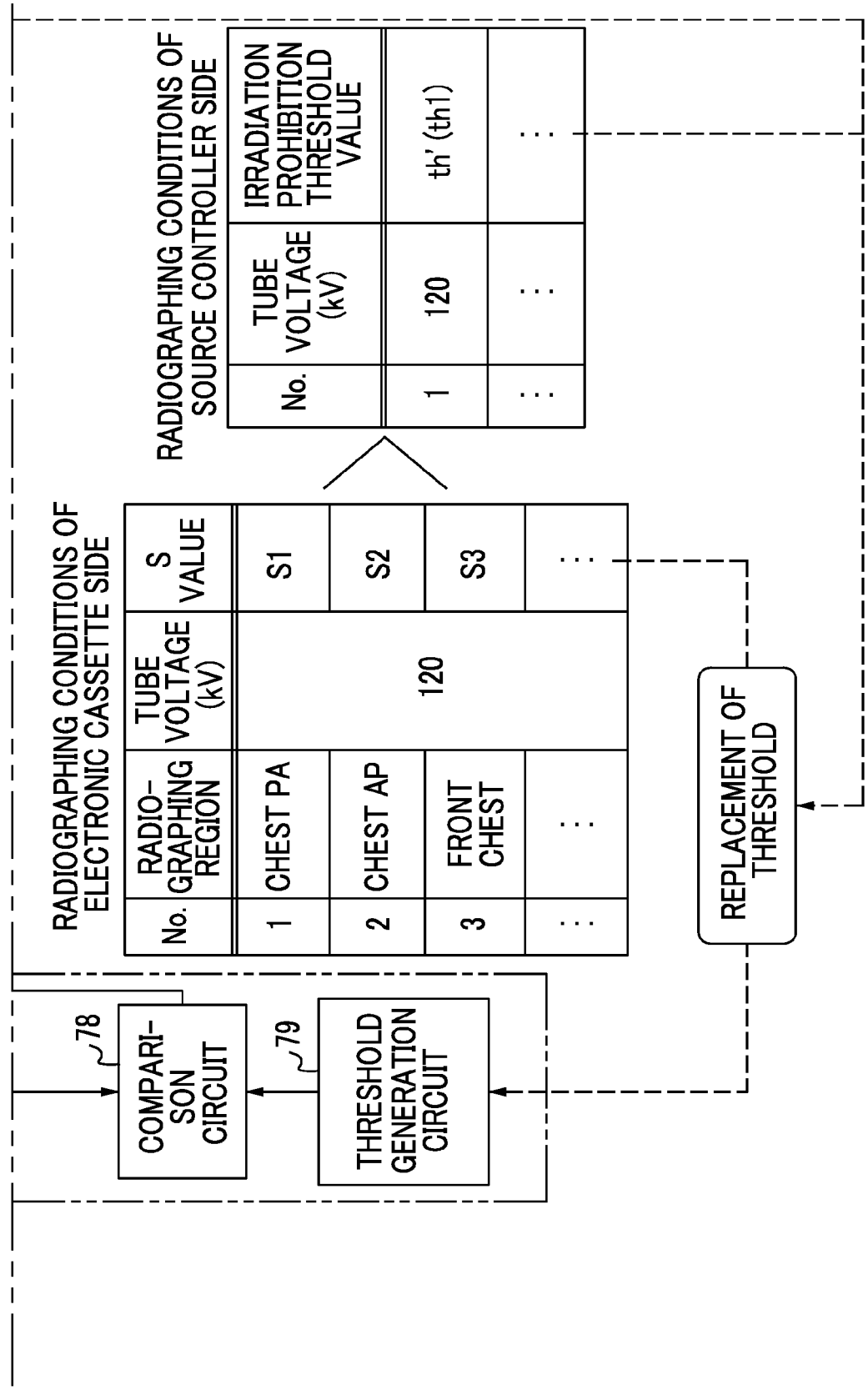

RADIOGRAPHIC SYSTEM, AUTOMATIC EXPOSURE CONTROL METHOD OF RADIOGRAPHIC SYSTEM, AND RADIOLOGICAL IMAGE DETECTOR

BACKGROUND OF THE PRESENT INVENTION

1. Field of the Present Invention

The present invention relates to a radiographic system, an automatic exposure control method of a radiographic system, and a radiological image detector.

2. Description of the Related Art

In the medical fields, radiographic systems using radiation such as X-rays are known. A radiographic system includes an X-ray generator generating X-rays and an X-ray imaging apparatus receiving X-rays and capturing an X-ray image. The X-ray generator includes an X-ray source irradiating an object with X-rays, a source controller controlling driving of the X-ray source, and an irradiation switch used to input an X-ray irradiation start instruction. The X-ray imaging apparatus includes an X-ray image detector receiving X-rays passing through an object and detecting an X-ray image and a console controlling driving of the X-ray image detector and performing various image processes on the X-ray image.

In the field of recent radiographic systems, X-ray image detectors using a flat panel detector (FPD) as a detection panel instead of an X-ray film or an imaging plate (IP) have been widespread. In the FPD, pixels accumulating signal charges corresponding to an amount of incident X-rays are arranged in a matrix shape. The FPD accumulates signal charges in the respective pixels and converts the accumulated signal charges into a voltage signal through the use of a signal processing circuit, whereby an X-ray image representing image information of the object is detected and is output as digital image data.

An electronic cassette (portable X-ray image detector) in which the FPD is built in a housing of a rectangular parallelepiped shape is also put into practice. Unlike a type fixed to a radiography platform and not detached therefrom, the electronic cassette is detachably attached to an existing radiography platform for a film cassette or an IP cassette or a dedicated radiography platform for use, or is placed on a bed in order to radiograph a site which is difficult to radiograph by the use of the fixed type or is made for an object to carry for use. The electronic cassette may be used in the outside of a hospital, in which there is no radiography platform, in order to radiograph an aged person under home remedy or an emergency patient under an accident or a disaster.

The radiographic system is provided with a sensor such as an ion chamber (ionization chamber) detecting an X-ray dose passing through an object and performs an automatic exposure control (AEC) stopping irradiation with X-rays from an X-ray source when the integrated value of the X-ray dose detected with the sensor reaches a predetermined threshold.

JP2003-302716A discloses that a phototimer (AEC sensor) is built in an electronic cassette and plural X-ray bulbs (X-ray sources) can be used to perform radiography by the use of the single phototimer. The output signal of the phototimer can be used as any of an X-ray blocking signal (irradiation stop signal) and an analog signal (detection signal, voltage value). In the former, charges from the phototimer are integrated in the electronic cassette, the integrated value and a threshold are compared, and the X-ray blocking signal is output when the integrated value is greater than the threshold. In the latter, analog signals are integrated in the receiving side (the X-ray generator side) and X-rays are blocked through the comparison with a threshold.

JP1995-201490A (JP-H07-201490A) discloses that a predetermined pixel among plural pixels is used as an X-ray exposure detecting pixel (AEC sensor).

SUMMARY OF THE PRESENT INVENTION

Some source controllers in the related art include an irradiation signal interface (I/F) (irradiation signal I/F) used to take synchronization with a reset process or an accumulation process which is performed at an irradiation start time by the electronic cassette side and an I/F (detection signal I/F) used to receive a detection signal from an AEC sensor according to the related art such as an ion chamber.

In general, when the AEC sensor according to the related art such as an ion chamber is used, there are plural sensors detecting X-rays in the AEC sensor, but a number of sensors of about three to five is standard. On the other hand, as disclosed in JP1995-201490A (JP-H07-201490A), in a detection panel using a pixel as an AEC sensor, since plural pixels to be used as the AEC sensor can be selected from plural pixels, the number of sensors can be made to be relatively large.

The source controllers are often made to correspond to the AEC sensor according to the related art such as an ion chamber. Accordingly, in many cases, radiographing conditions and an irradiation-stop threshold which can be set by the source controller side depend on the number of sensors and have smaller variations than those which can be set by the electronic cassette side. Therefore, since the electronic cassette side can have more variations of the radiographing conditions and the radiographing conditions can be finely optimized, an X-ray image with relatively good image quality can be obtained by allowing the electronic cassette side to determine the irradiation stop with X-rays and to exchange an irradiation stop signal. By allowing the electronic cassette side to determine the irradiation stop of X-rays and to exchange an irradiation stop signal, the process of causing the source controller side to integrate a detection signal and stopping the irradiation with X-rays is made to be unnecessary and the AEC is finished in the electronic cassette, whereby there are merits that the design is simple, it is easy to secure operation quality as a system, and an error hardly occurs during use. Here, the exchange part exchanging of information such as communication, delivery, and transmission.

On the contrary, the irradiation signal I/F causes various problems in connection work. Specifically, when manufacturers of the X-ray generator and the X-ray imaging apparatus are different, specifications of cables or connectors of the irradiation signal I/F of the source controller and the electronic cassette, types of the irradiation stop signal, and the like are not suitable and thus the connection may be difficult or may not be possible.

On the other hand, the detection signal I/F is often made to relatively simply perform the connection work such that any manufacturer is able to connect the X-ray generator to the AEC sensor according to the related art at a later time. However, on the contrary to the irradiation signal I/F, the source controller side having small variations of radiographing conditions determines the irradiation stop with X-rays and thus the image quality of an X-ray image may be lower in comparison with a case where the irradiation signal I/F is used.

In this way, the exchange of an irradiation stop signal using the irradiation signal I/F and the exchange of a detection signal using the detection signal I/F have both merits and demerits. JP2003-302716A describes that any of the irradiation stop signal and the detection signal may be output, but does not describe which should be selected and output in what situation. Accordingly, an interface unsuitable for the situation may be selected and may adversely affect the radiography or the later diagnosis.

The present invention is made in consideration of the above-mentioned circumstances and an object thereof is to provide a radiographic system, an automatic exposure control method of the radiographic system, and a radiological image detector, which can perform an AEC suitable for a situation.

According to an aspect of the present invention, there is provided a radiographic system having a radiation source that irradiates an object with radiation, a source controller that controls the radiation source, and a radiological image detector that receives the radiation passing through the object to detect a radiological image and that has an AEC sensor performing an automatic exposure control of detecting the dose of the radiation passing through the object and stopping irradiation with the radiation from the radiation source when the integrated value of the detected dose reaches a predetermined irradiation-stop threshold, the radiographic system implementing the automatic exposure control by exchanging any one of a detection signal of the AEC sensor and an irradiation stop signal based on a comparison result of the integrated value of the detection signal of the AEC sensor and the irradiation-stop threshold between the source controller and the radiological image detector, the radiographic system including: an information acquiring part for acquiring type information on an installation convenience preference type in which convenience in connection between the source controller and the radiological image detector is preferred or an installation convenience non-preference type; and a switching part for selectively switching an output format of an automatic exposure control signal so as to exchange the detection signal between the source controller and the radiological image detector when the type acquired by the information acquiring part is the installation convenience preference type and to exchange the irradiation stop signal between the source controller and the radiological image detector when the type acquired by the information acquiring part is the installation convenience non-preference type.

The radiographic system may further include a first storage part for storing source information in which a source ID specific to the radiation source and a type are correlated with each other, and the information acquiring part may acquire the type information by acquiring a source ID and retrieving and extracting the type correlated with the acquired source ID from the source information. The source information preferably includes the type for each region of shipment.

Alternatively, the radiographic system may further include: a display part for displaying a GUI receiving an input of the type; and an input device to which the type is input through the use of the GUI, and the information acquiring part may acquire the type information from the input result of the type through the input device.

The radiological image detector may include a detection signal I/F outputting the detection signal and an irradiation signal I/F outputting the irradiation stop signal. The switching part may be disposed in the radiological image detector. The switching part may select the detection signal I/F as the output destination of the automatic exposure control signal when the type acquired by the information acquiring part is the installation convenience preference type, and may select the irradiation signal I/F as the output destination of the automatic exposure control signal when the type acquired by the information acquiring part is the installation convenience non-preference type.

The radiographic system may further include a converter that is connected to both the source controller and the radiological image detector and that relays exchange of the signals, and the switching part may be disposed in the converter. The radiological image detector may include only a detection signal I/F outputting the detection signal, and the converter may include an irradiation signal I/F outputting the irradiation stop signal in addition to a detection signal I/F. The switching part may select the detection signal I/F as the output destination of the automatic exposure control signal when the type acquired by the information acquiring part is the installation convenience preference type and may select the irradiation signal I/F as the output destination of the automatic exposure control signal when the type acquired by the information acquiring part is the installation convenience non-preference type.

The information acquiring part may acquire the type information when the AEC sensor attached to the radiological image detector is connected to the source controller for use instead of an AEC sensor (an old AEC sensor) used hitherto.

The information acquiring part may acquire positional information of a detection field of the old AEC sensor. The radiographic system may further include a detection field selecting part for selecting a detection field of the AEC sensor so as to match the detection field of the old AEC sensor on the basis of the positional information of the detection field of the old AEC sensor. The detection field selecting part may select the detection field depending on the posture of the radiological image detector.

The radiographic system may further include a correction part for correcting the detection signal of the AEC sensor to a detection signal corresponding to the detection signal of the old AEC sensor so as to exclude the influence on the detection signal due to a variation in constitution of an intermediate member which is disposed between the radiation source and an imaging plane of a detection panel of the radiological image detector when the AEC sensor is used instead of the old AEC sensor.

The radiographic system may further include a second storage part for storing a correlation between the detection signal of the AEC sensor and the detection signal of the old AEC sensor, and the correction part may perform the correction on the basis of the correlation between the detection signal of the AEC sensor and the detection signal of the old AEC sensor. Here, the intermediate member may include at least one of a housing covering the detection panel of the radiological image detector, a scintillator converting radiation into visible rays, and a grid removing radiation scattered in the object.

The radiographic system may further include an integration part for integrating the detection signal output from the correction part. The information acquiring part may acquire information on whether the source controller has a function of integrating the detection signal. The switching part may output the detection signal output from the correction part without passing through the integration part when the type acquired by the information acquiring part is the installation convenience preference type and the source controller has the function of integrating the detection signal, and may output the integrated value of the detection signal output from the integration part when the source controller does not have the function of integrating the detection signal.

The information acquiring part may acquire the irradiation-stop threshold set by the source controller. The radiographic system may further include a comparison part for comparing the integrated value of the detection signal output from the integration part with the irradiation-stop threshold set by the source controller and outputting the irradiation stop signal when the integrated value of the detection signal reaches the irradiation-stop threshold.

The detection field selecting part, the correction part, the integration part, and the comparison part may be disposed in the radiological image detector or the converter.

When the type acquired by the information acquiring part is the installation convenience non-preference type, an inquiry signal for inquiring whether the irradiation of radiation should be started and an irradiation permission signal permitting the irradiation of radiation may be exchanged between the source controller and the radiological image detector.

The AEC sensor attached to the radiological image detector may be a pixel directly connected to a signal line for reading signal charges without using a switching element. The radiological image detector may be an electronic cassette in which a detection panel is received in a portable housing.

According to another aspect of the present invention, there is provided an automatic exposure control method of a radiographic system having a radiation source that irradiates a object with radiation, a source controller that controls the radiation source, and a radiological image detector that receives the radiation passing through the object to detect a radiological image and that has an AEC sensor performing an automatic exposure control of detecting the dose of the radiation passing through the object and stopping irradiation with the radiation from the radiation source when the integrated value of the detected dose reaches a predetermined irradiation-stop threshold, the radiographic system implementing the automatic exposure control by exchanging any one of a detection signal of the AEC sensor and an irradiation stop signal based on a comparison result of the integrated value of the detection signal of the AEC sensor and the irradiation-stop threshold between the source controller and the radiological image detector, the automatic exposure control method including: an information acquiring step of acquiring type information on an installation convenience preference type in which convenience in connection between the source controller and the radiological image detector is preferred or an installation convenience non-preference type; and a switching step of selectively switching an output format of an automatic exposure control signal so as to exchange the detection signal between the source controller and the radiological image detector when the type acquired in the information acquiring step is the installation convenience preference type and to exchange the irradiation stop signal between the source controller and the radiological image detector when the type acquired by the information acquiring part is the installation convenience non-preference type.

According to still another aspect of the present invention, there is provided a radiological image detector that receives radiation passing through an object to detect a radiological image, including: an AEC sensor that performs an automatic exposure control of detecting the dose of the radiation passing through the object and stopping irradiation with the radiation from a radiation source when the integrated value of the detected dose reaches a predetermined irradiation-stop threshold, wherein the automatic exposure control is implemented by exchanging any one of a detection signal of the AEC sensor and an irradiation stop signal based on a comparison result of the integrated value of the detection signal of the AEC sensor and the irradiation-stop threshold with a source controller controlling the radiation source, and wherein an output format of an automatic exposure control signal is selectively switched so as to exchange the detection signal with the source controller and the radiological image detector in the case of an installation convenience preference type in which convenience in connection to the source controller is preferred and to exchange the irradiation stop signal with the source controller in the case of an installation convenience non-preference type.

According to the aspects of the present invention, since the output format of an automatic exposure control signal is selectively switched to a detection signal or an irradiation stop signal depending on the installation convenience preference type or the installation convenience non-preference type, it is possible to perform an AEC suitable for a situation.

BRIEF DESCRIPTION OF THE DRAWINGS

FIG. 3 is a block diagram illustrating the internal constitution of an electronic cassette.

FIG. 6 is a diagram illustrating radiographing conditions set in a console.

FIG. 9 is a diagram illustrating source information.

FIG. 10 is a comparison table illustrating regional types of installation convenience preference and installation convenience non-preference.

DESCRIPTION OF THE PREFERRED EMBODIMENTS

Figure 1:
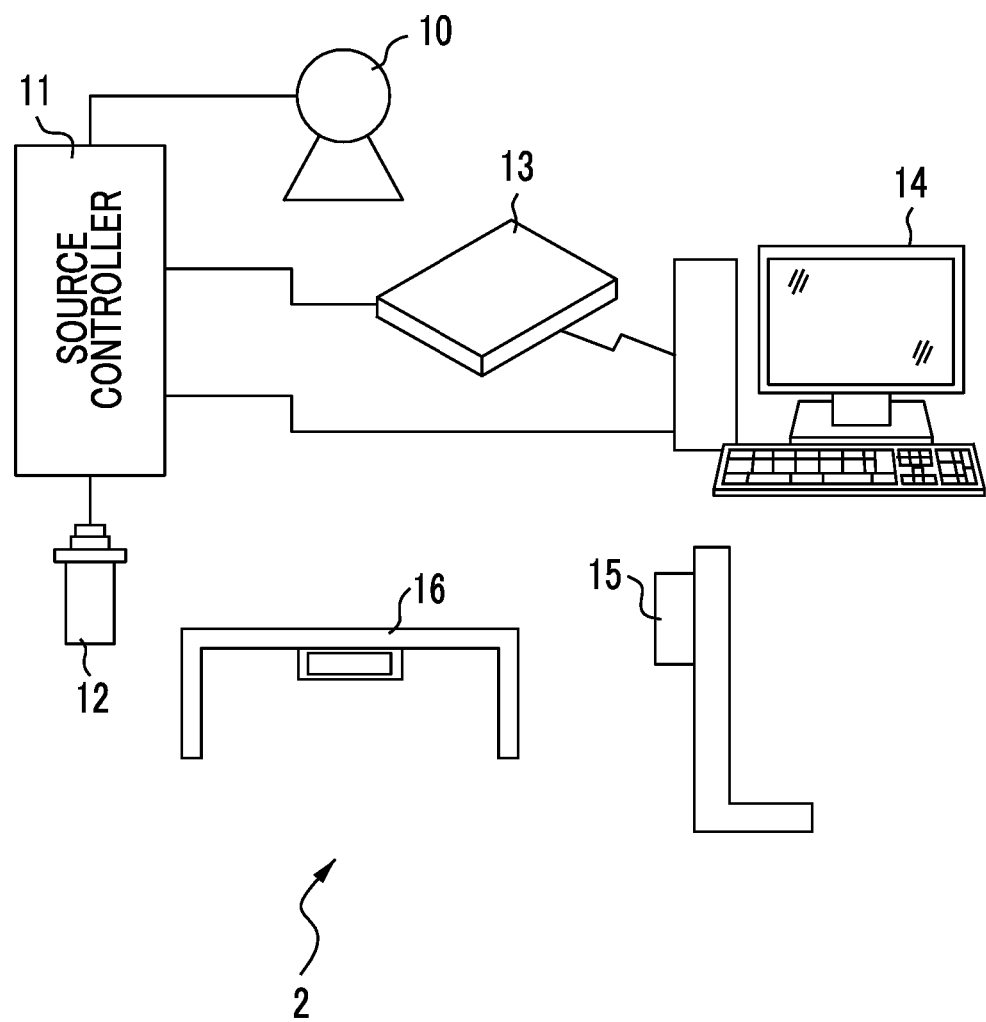
FIG. 1 is a diagram schematically illustrating the configuration of a radiographic system.

In FIG. 1, the radiographic system 2 includes an X-ray source 10 having an X-ray tube radiating X-rays therein, a source controller 11 controlling the operation of the X-ray source 10, an irradiation switch 12 instructing the irradiation start of X-rays, an electronic cassette 13 detecting X-rays passing through an object and outputting an X-ray image, a console 14 performing the operation control of the electronic cassette 13 or an image process on the X-ray image, an upright radiography platform 15 radiographing the object with an upright posture, and a decubitus radiography platform 16 radiographing the object with a decubitus posture. The X-ray source 10, the source controller 11, and the irradiation switch 12 constitute an X-ray generator and the electronic cassette 13 and the console 14 constitute an X-ray imaging apparatus. In addition, a source moving mechanism (not shown) used to set the X-ray source 10 at a desired direction and a desired position and the like are provided. The source controller 11 and the console 14 may be formed as a body.

The X-ray source 10 includes an X-ray tube radiating X-rays and an irradiation field limiter (collimator) limiting the irradiation field of X-rays radiated from the X-ray tube. The X-ray tube includes a negative electrode formed of a filament emitting thermal electrons and a positive electrode (target) with which the thermal electrons emitted from the negative electrode collide to radiate X-rays. The irradiation field limiter includes plural lead strips blocking X-rays, which are arranged in a parallel-crosses shape and in which an irradiation aperture transmitting X-rays is formed at the center thereof, and moves the positions of the lead strips to change the size of the irradiation aperture and to limit the irradiation field.

Figure 2:
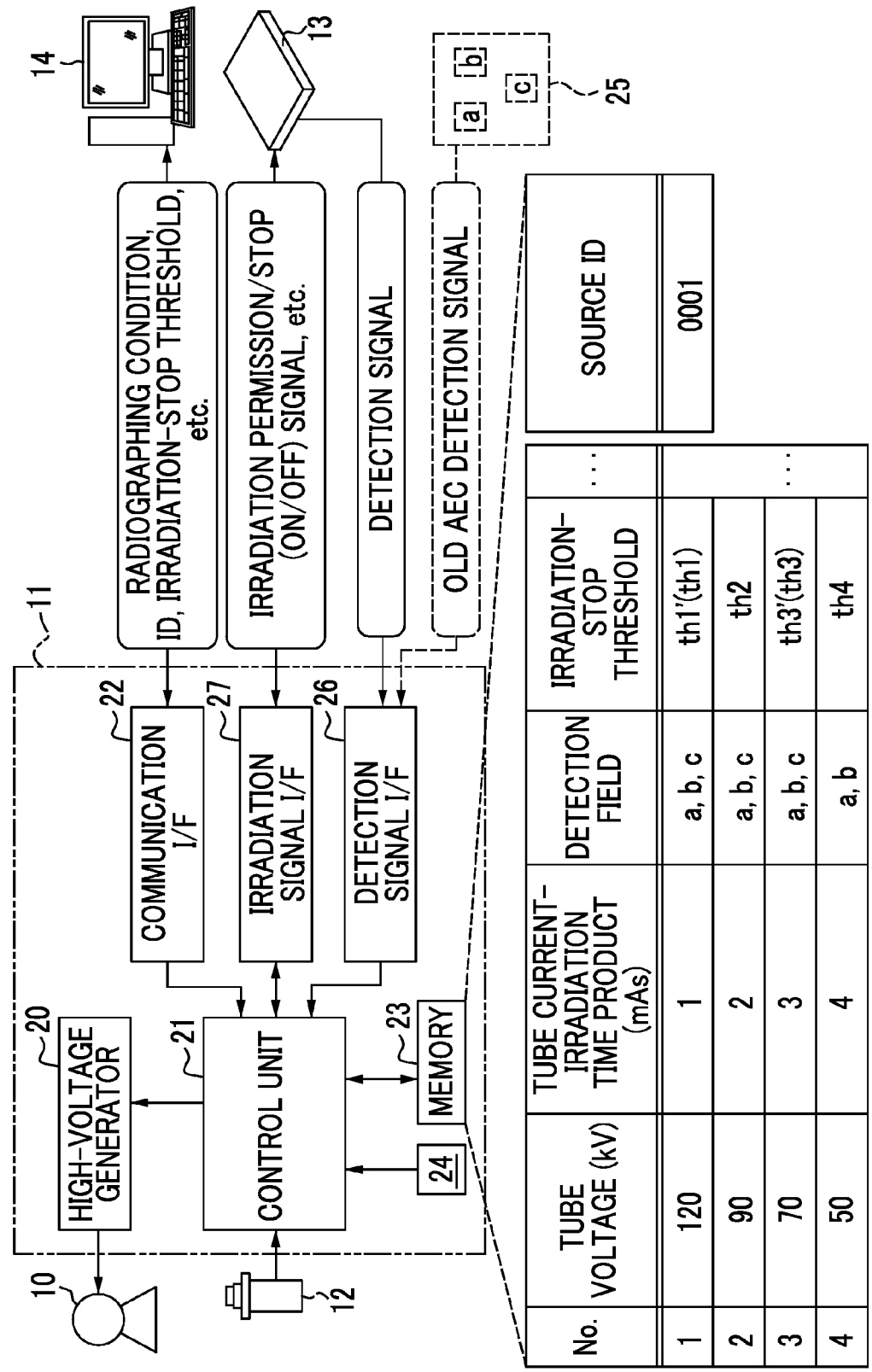
FIG. 2 is a diagram illustrating the internal constitution of a source controller and connections between the source controller and other devices.

As shown in FIG. 2, the source controller 11 includes a high voltage generator 20 raising an input voltage through the use of a transformer to generate a high tube voltage and supplying the high voltage to the X-ray source 10 via a high-voltage cable, a control unit 21 controlling a tube voltage used to determine an energy spectrum of X-rays radiated from the X-ray source 10, a tube current used to determine the exposure dose per unit time, and the irradiation time of X-rays, and a communication I/F 22 relaying important information with the console 14 and transmitting and receiving signals.

An irradiation switch 12, a memory 23, and a touch panel 24 are connected to the control unit 21. The irradiation switch 12 is, for example, a two-step push switch manipulated by an operator such as a radiographer, generates a warm-up start signal for starting warming-up of the X-ray source 10 by the first-step push, and generates an irradiation start signal for starting the irradiation from the X-ray source 10 by the second-step push. These signals are input to the source controller 11 via a signal cable. The control unit 21 starts the supply of power from the high voltage generator 20 to the X-ray source 10, when receiving the irradiation start signal from the irradiation switch 12.

The memory 23 stores plural types of radiographing conditions such as a tube voltage and a tube current-irradiation time product (value in mAs) in advance. In this example, a tube current-irradiation time product, the detection field of an AEC sensor (also referred to as an old AEC sensor) 25 disposed in the X-ray source 10, and an irradiation-stop threshold value used to determine the irradiation stop with X-rays in comparison with the integrated value of a detection signal (a value obtained by converting the dose of incident X-rays in terms of a voltage, which is referred to as an old AECV detection signal) of the old AEC sensor 25, and the like are stored for each No. as a radiographing condition and for each tube voltage (four types of 120 kV of No. 1, 90 kV of No. 2, 70 kV of No. 3, and 50 kV of No. 4). In the irradiation-stop threshold value, values (default values) th1 to th4 determined at the time of shipment of the X-ray source 10 are set in advance. As in 120 kV of No. 1 and 70 kV of No. 3, when the default value is adjusted by an operator in use, both the adjusted value and the default value are stored. The radiographing conditions are manually set by an operator through the use of the touch panel 24 by designating the No. or the like. The source controller 11 is expected to radiate X-rays with the tube voltage or the tube current-irradiation time product correlated with the designated radiographing condition No. The AEC serves to stop the irradiation with X-rays when it is detected that a necessary and sufficient dose is reached, even when the tube current-irradiation time product (irradiation time) is lower than or equal to the tube current-irradiation time product with which the source controller 11 is expected to radiate X-rays. In order to prevent the lack of dose due to the end of the irradiation with X-rays before a target dose is reached and the irradiation stop is determined by the AEC, the maximum value of the tube current-irradiation time product (irradiation time) is set in the radiographing condition of the X-ray source 10.

The memory 23 also stores an ID (source ID) specific to the X-ray source 10. The control unit 21 transmits the source ID read from the memory 23 along with the information of the irradiation-stop threshold value of the radiographing condition to the console 14 via the communication I/F 22, when the installation of the source controller is finished and communications with the console 14 are set up.

The old AEC sensor 25 includes an ion chamber (ionization chamber) known in the related art and outputs an old AEC detection signal corresponding to the incident dose. The old AEC sensor 25 has approximately the same two-dimensional size as a cassette used in the radiographic system and is used in a state where it is placed in front of an imaging plane of the cassette. The old AEC sensor 25 is provided with three detection fields a, b, and c in total of the upper left and right sides corresponding to the lungs in the radiography of a chest and the lower center. The item of detection field in the radiographing conditions of FIG. 2 indicates what of these three light fields a to c should be used.

The old AEC sensor 25 is connected to a detection signal I/F 26. The old AEC detection signal is input to the control unit 21 via the detection signal I/F 26. The input old AEC detection signal is the integrated value of the old AEC detection signal when the old AEC sensor 25 includes an integration circuit, and is the old AEC detection signal itself (instantaneous value) when the old AEC sensor does not include an integration circuit. In the latter, the control unit 21 includes an integration circuit and the control unit 21 integrates the old AEC detection signal. In this example, since the old AEC sensor 25 includes an integration circuit and the control unit 21 does not include an integration circuit (see FIG. 9), the integrated value of the old AEC detection signal is input to the control unit 21. The instantaneous value or the integrated value of the old AEC detection signal sent from the old AEC sensor 25 may be a value for each light field or may be a total value or an average value of the detection fields.

The control unit 21 starts monitoring the integrated value of the old AEC detection signal when receiving the irradiation start signal from the irradiation switch 12. The control unit 21 compares the integrated value with the irradiation-stop threshold value set in the radiographing conditions at an appropriate time. Subsequently, when X-rays are radiated from the X-ray source 13 and the integrated value reaches the irradiation-stop threshold value, the control unit 21 transmits the irradiation stop signal instructing to stop the irradiation with X-rays to the high voltage generator 20. The high voltage generator 20 stops the supply of power to the X-ray source 15 in response to the irradiation stop signal and stops the irradiation with X-rays.

The irradiation signal I/F 27 is provided, unlike the communication I/F 22 and the detection signal I/F 26, when the irradiation start time of X-rays is prescribed or when the irradiation stop time of X-rays is prescribed in a constituent other than the old AEC sensor 25 outputting a voltage value. An AEC sensor having the same function as the old AEC sensor 25 and the control unit 21 or an electronic cassette having the same function as the old AEC sensor 25 and the control unit 21, such as the electronic cassette 13 in this example, is connected to the irradiation signal I/F 27.

When the electronic cassette having the same functions as the old AEC sensor 25 and the control unit 21 is connected to the irradiation signal I/F 27 and the warm-up start signal is received from the irradiation switch 12, the control unit 21 transmits an inquiry signal to the electronic cassette via the irradiation signal I/F 27. When receiving the inquiry signal, the electronic cassette ends a reset process to be described later or performs a preliminary process such as an accumulation starting process. When an irradiation permission signal as a response to the inquiry signal is received from the electronic cassette via the irradiation signal I/F 27 and the irradiation start signal is received from the irradiation switch 12, the control unit 21 starts the supply of power to the X-ray source 10 from the high voltage generator 20. When an irradiation stop signal transmitted from the AEC sensor or the electronic cassette having the same functions as the old AEC sensor 25 and the control unit 21 is received via the irradiation signal I/F 27, the control unit 21 stops the supply of power to the X-ray source 10 from the high voltage generator 20 to stop the irradiation with X-rays. In the drawing, for the purpose of convenient explanation, both the detection signal I/F 26 and the irradiation signal I/F 27 are connected to the electronic cassette 13, but any one is used for the actual process of stopping the irradiation with X-rays and both are not used simultaneously.

In FIG. 3, the electronic cassette 13 includes a flat panel detector (FPD) 35 and a portable housing containing the FPD 35 as widely known. The housing of the electronic cassette 13 has approximately a flat rectangular shape and the two-dimensional size thereof is the same size (the size based on the international standard ISO 4090; 2001) as a film cassette or an IP cassette (also referred to as a CR cassette). Accordingly, the electronic cassette can be mounted on an existing radiography platform for the film cassette or the IP cassette.

Plural electronic cassettes 13, for example, two electronic cassettes for the upright radiography platform 15 and the decubitus radiography platform 16, are disposed in one radiography room in which the radiographic system 2 is installed. The electronic cassettes 13 are detachably set on the upright radiography platform 15 and the decubitus radiography platform 16 so that the imaging plane 36 of the FPD 35 is maintained to oppose the X-ray source 10. The electronic cassettes 13 may be used as a single body by placing the electronic cassette on a bed on which an object lies or causing an object to carry the electronic cassette, instead of setting the electronic cassette on the upright radiography platform 15 or the decubitus radiography platform 16.

The electronic cassette 13 has an antenna 37 and a battery 38 built therein and can wirelessly communicate with the console 14. The antenna 37 transmits and receives electric waves for wireless communication to and from the console 14. The battery 38 supplies power for operating the constituents of the electronic cassette 13. Regarding the battery 38, a small battery is used so as to enter the thin electronic cassette 13. The battery 38 may be taken out of the electronic cassette 13, may be set in a dedicated cradle, and may be charged. The battery 38 may be configured to be wirelessly power suppliable.

The electronic cassette 13 is provided with a socket 39 in addition to the antenna 37. The socket 39 is disposed for wired connection to the console 14 and is used when the wireless communication between the electronic cassette 13 and the console 14 is not possible due to a lack of capacity of the battery 38 or the like. When a cable from the console 14 is connected to the socket 39, the wired communication with the console 14 becomes possible. At this time, power may be supplied from the console 14 to the electronic cassette 13.

The antenna 37 and the socket 39 are connected to a communication unit 40. The communication unit 40 relays transmission and reception of a variety of information and signals including image data between the antenna 37 or the socket 39 and the control unit 41 and the memory 42.

The FPD 35 has a TFT active matrix substrate and also includes an imaging plane 36 in which plural pixels 45 accumulating signal charges corresponding to the incident dose of X-rays are arranged on the substrate. The plural pixels 45 are two-dimensionally arranged in a matrix shape of n rows (x direction)×m columns (y direction) at predetermined pitches.

The FPD 35 further includes a scintillator (fluorescent substance) converting X-rays into visible rays and is of an indirect conversion type photoelectrically converting the visible rays converted by the scintillator by the use of the pixels 45. The scintillator is formed of CsI (cesium iodide), GOS (gadolinium oxysulfide), or the like, and is disposed to oppose the front surface of the imaging plane 36 on which the pixels 45 are arranged. The scintillator and the FPD 35 may be a PSS (Penetration Side Sampling) type in which the scintillator and the FPD 35 are arranged in this order when seen from the incidence side of X-rays, or may be an ISS (Irradiation Side Sampling) type in which the FPD 35 and the scintillator are arranged in this order to the contrary. A direct conversion type FPD employing a conversion layer (amorphous selenium) directly converting X-rays into charges instead of the scintillator may be used.

Each pixel 45 includes a photodiode 46 which is a photoelectric conversion element generating charges (electron-hole pairs) in response to the incidence of visible rays, a capacitor (not shown) accumulating the charges generated from the photodiode 46, and a thin film transistor (TFT) 47 as a switching element.

The photodiode 46 has a structure in which a semiconductor layer (for example, PIN type) generating charges and an upper electrode and a lower electrode disposed on and under the semiconductor layer are arranged. In the photodiode 46, the TFT 47 is connected to the lower electrode and a bias line 48 is connected to the upper electrode. The bias lines 48 corresponding to the number of rows (n rows) of the pixels 45 in the imaging plane 36 are disposed and are connected to a connection line 49. The connection line 49 is connected to a bias power source 50. A bias voltage Vb is applied from the bias power source 50 to the upper electrode of the photodiode 46 via the connection line 49 and the bias line 48. An electric field is generated in the semiconductor layer with the application of the bias voltage Vb and charges (electron-hole pairs)

generated in the semiconductor layer through the photoelectric conversion move to the upper electrode and the lower electrode of which one has a plus polarity and the other has a minus polarity, and the charges are accumulated in the capacitor.

In the TFT 47, the gate electrode is connected to a scanning line 51, the source electrode is connected to a signal line 52, and the drain electrode is connected to a photodiode 46. The scanning lines 51 and the signal lines 52 are wired in a lattic shape, the number of scanning lines 51 corresponds to the number of rows (n rows) of the pixels 45 in the imaging plane 36, and the number of signal lines 52 corresponds to the number of columns (m columns) of the pixels 45. The scanning lines 51 are connected to a gate driver 53 and the signal lines 52 are connected to a signal processing circuit 54.

The gate driver 53 drives the TFT 47 to perform an accumulating operation of accumulating signal charges corresponding to the incident dose of X-rays in the pixels 45 and to perform a reading (main reading) operation and a reset (idle reading) operation of reading the signal charges from the pixels 45. The control unit 41 controls the start times of the operations performed by the gate driver 53.

In the accumulating operation, the TFTs 47 are turned off and the signal charges are accumulated in the pixels 45 in the meantime. In the reading operation, gate pulses G1 to Gn driving the TFTs 47 in the same row at a time are sequentially generated from the gate driver 53 to sequentially activate the scanning lines 51 row by row and the TFTs 47 connected to the scanning lines 51 are turned on row by row. The charges accumulated in the capacitors of the pixels 45 are read to the signal lines 52 when the corresponding TFTs 47 are turned on, and are input to the signal processing circuit 54.

Dark charges are generated in the semiconductor layer of the photodiode 46 regardless of the incidence of X-rays. Since the bias voltage Vb is applied, the dark charges are accumulated in the corresponding capacitor. Since the dark charged generated in the pixels 45 serve as noise components in image data, a reset operation is performed to remove the dark charges. The reset operation is an operation of sweeping out the dark charges generated in the pixels 45 through the use of the signal lines 52.

The reset operation is performed, for example, in a sequential reset type of resetting the pixels 45 row by row. In the sequential reset type, similarly to the operation of reading the signal charges, gate pulses G1 to Gn are sequentially generated from the gate driver 53 to the scanning lines 51 to turn on the TFTs 47 of the pixels 45 row by row. When the TFT 47 is turned on, the dark charges flow from the corresponding pixel 45 to an integration amplifier 60 via the corresponding signal line 52. In the reset operation, unlike the reading operation, the reading of the charges accumulated in the integration amplifiers 60 by a multiplexer (MUX) 61 is not performed and a reset pulse RST is output from the control unit 41 in synchronization with the generation of the gate pulses G1 to Gn to reset the integration amplifiers 60.

Instead of the sequential reset type, a parallel reset type of sequentially resetting groups, each of which include plural rows of pixels, and simultaneously sweeping out the dark charges of the rows in the corresponding group or an overall pixel reset type of giving a gate pulse to the overall rows and simultaneously sweeping out the dark charges of all the pixels may be used. It is possible to raise the speed of the reset operation by using the parallel reset type or the overall pixel reset type.

The signal processing circuit 54 includes integration amplifiers 60, a MUX 61, and an A/D converter 62. The integration amplifiers 60 are individually connected to the signal lines 52. Each integration amplifier 60 includes an operational amplifier and a capacitor connected between input and output terminals of the operational amplifier. The signal line 52 is connected to one input terminal of the operational amplifier. The other input terminal of the integration amplifier 60 is connected to the ground (GND). The integration amplifiers 60 integrate the charges input from the signal lines 52, convert the integrated charges into voltage signals D1 to Dm, and output the voltage signals. The MUX 61 is connected to the output terminal of the integration amplifier 60 of each column via amplifiers 63, sampling and holding (S/H) units 64. The A/D converter 62 is connected to the output side of the MUX 61.

The MUX 61 sequentially selects one integration amplifier 60 from the plural integration amplifiers 60 connected in parallel and serially inputs the voltage signals D1 to Dm output from the selected integration amplifier 60 to the A/D converter 62. The A/D converter 62 converts the input voltage signals D1 to Dm to digital data and outputs the digital data to the memory 42 built in the electronic cassette 13. An amplifier may be connected between the MUX 61 and the A/D converter 62.

When the voltage signals D1 to Dm corresponding to one row are read from the integration amplifiers 60 by the MUX 61, the control unit 41 outputs a reset pulse RST to the integration amplifiers 60 and turns on a reset switch 60$a$ of the integration amplifier 60. Accordingly, the signal charges of one row accumulated in the integration amplifiers 60 are reset. When the integration amplifiers 60 are reset, the gate pulse of the next row is output from the gate driver 53 and the reading of signal charges in the pixels 45 of the next row is started. By sequentially repeating these operations, the signal charges in the pixels 45 of all the rows are read.

When the signal charges of all the rows are read, image data indicating an X-ray image of one screen is recorded in the memory 42. The image data is read from the memory 42 and is output to the console 14 via the communication unit 40. In this way, the X-ray image of an object is detected.

When the irradiation signal I/F 27 is present, the control unit 41 of the electronic cassette 13 controls the FPD 35 to perform the reset operation and to return an irradiation permission signal to the source controller 11, at the time of receiving the inquiry signal from the control unit 21 of the source controller 11. Then, the operation of the FPD 35 is switched from the reset operation to the accumulating operation at the time of receiving the irradiation start signal. When the irradiation signal I/F 27 is not present, the FPD 35 detects the irradiation start with X-rays is detected by the use of detection pixels 65 to be described later while repeatedly performing the reset operation. When the irradiation start with X-rays is detected, the control unit 41 switches the operation of the FPD 35 from the reset operation to the accumulating operation. When the irradiation stop with X-rays is detected by the detection pixels 65, the operation of the FPD 35 is switched from the accumulating operation to the reading operation.

The FPD 35 includes plural detection pixels 65, which are short-circuited to the signal lines 52 without passing through the TFTs 47, in the same imaging plane 36 in addition to the pixels 45 connected to the signal lines 52 via the TFTs 47 as described above. A detection pixel 65 is a pixel used to detect the dose of X-rays passing through an object and incident on the imaging plane 36 and serves as an irradiation start sensor or serves as an irradiation end detection sensor and an AEC sensor. The detection pixels 65 occupy several % of the pixels 45 in the imaging plane 36.

Figure 4:
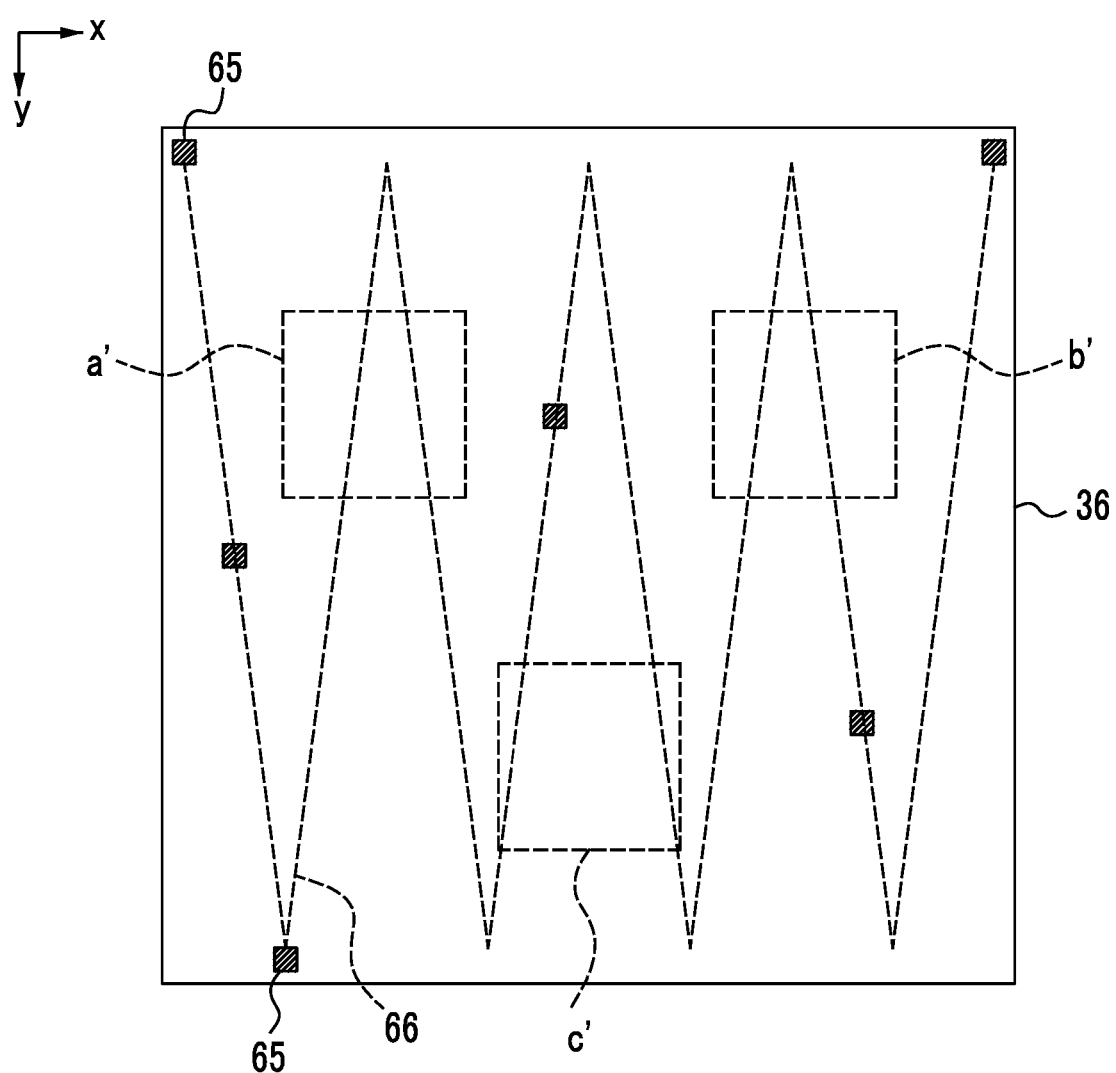
FIG. 4 is a diagram illustrating the arrangement of detection pixels of an FPD of the electronic cassette.

As shown in FIG. 4, the detection pixels 65 are arranged in a waveform locus 66 indicated by a dotted line symmetric about the center of the imaging plane 36 so as to be evenly scattered in the imaging plane 36 without locally deviating in the imaging plane 36. The detection pixel 65 is provided for each column of the pixels 45 connected to the same signal line 52. The columns having the detection pixel 65 are arranged, for example, every two or three columns in which the detection pixel 65 is not disposed. The positions of the detection pixels 65 are known at the time of manufacturing the FPD 35. The FPD 35 stores the positions (coordinates) of all the detection pixels 65 in a nonvolatile memory (not shown).

Since the detection pixel 65 does not include the TFT 47 between the corresponding signal line 52 and the detection pixel and is directly connected to the corresponding signal line 52, the signal charges generated from the detection pixels 65 are read to the signal line 52 at once. The same is also true when the pixels 45 in the same column are performing the accumulating operation of accumulating by turning off the TFTs 47. Accordingly, the charges generated from the detection pixel 65 always flows in the integration amplifier 60 in the signal line 52 connected to the detection pixel 65.

Figure 5:
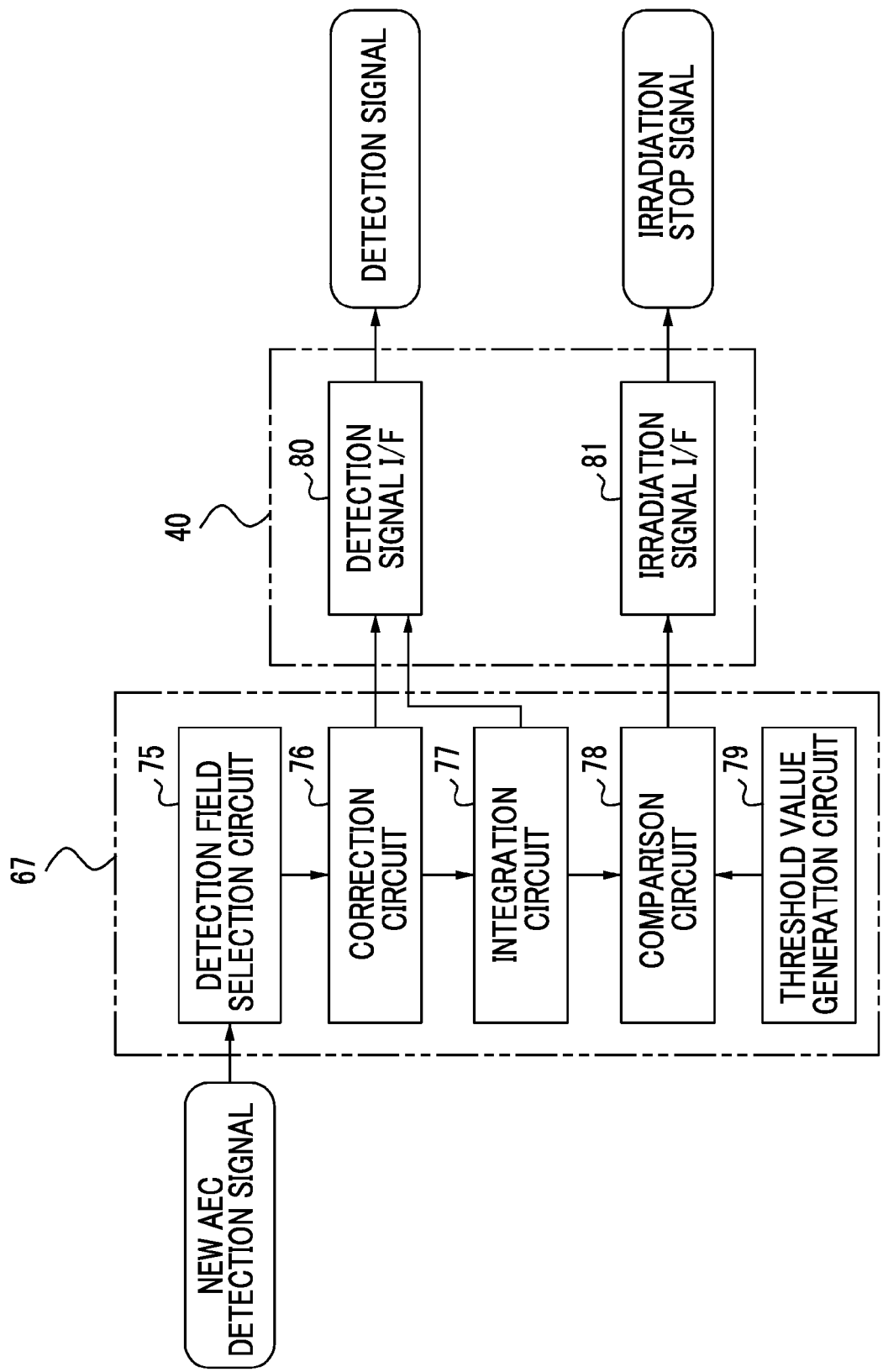
FIG. 5 is a block diagram illustrating the internal constitutions of an AEC unit and a communication unit of the electronic cassette.

The AEVC unit 67 acquires a voltage value (referred to as a new AEC detection signal) from the signal line 52 connected to the detection pixel 65 via the A/D converter 62. In FIG. 5, the AEC unit 67 includes a detection field selecting circuit 75, a correction circuit 76, an integration circuit 77, a comparison circuit 78, and a threshold generating circuit 79. The AEC unit 67 further includes an irradiation start and end detection circuit detecting the start and end of the irradiation start with X-rays by comparing the new AEC detection signal from the detection pixel 65 with a predetermined threshold value.

The detection field selecting circuit 75 selects a detection pixels 65 of which the new AEC detection signal should be used in the AEC among plural detection pixels 65 scattered in the imaging plane 36. The correction circuit 76 corrects the new AEC detection signal to a value (referred to as a detection signal) corresponding to the old AEC detection signal. The integration circuit 77 integrates the detection signal. The comparison circuit 78 starts monitoring the integrated value of the detection signal from the integration circuit 77 when the irradiation start with X-rays is detected. The integrated value is compared with the irradiation-stop threshold value (which is the same as the irradiation-stop threshold value of the source controller 11) given from the threshold generating circuit 79 at an appropriate time. When the integrated value reaches the threshold value, the comparison circuit 78 outputs the irradiation stop signal.

The communication unit 40 is provided with a detection signal I/F 80 and an irradiation signal I/F 81. The detection signal I/F 26 of the source controller 11 is connected to the detection signal I/F 80 via a signal cable and the irradiation signal I/F 27 of the source controller 11 is connected to the irradiation signal I/F 81 via a signal cable. The correction circuit 76 and the integration circuit 77 of the AEC unit 67 are connected to the detection signal I/F 80. One of the output of correction circuit 76, that is, the detection signal of the new AEC detection signal, and the output of the integration circuit 77, that is, the integrated value of the detection signal, is selectively output from the detection signal I/F 80. The irradiation signal I/F 81 receives an inquiry signal, transmits the irradiation permission signal in response to the inquiry signal, and transmits the output of the comparison circuit 78, that is, the irradiation stop signal. Like the source controller 11, any one of the detection signal I/F 80 and the irradiation signal I/F 81 is used in the process of stopping the irradiation with X-rays, but both is not simultaneously used.

The console 14 is connected to the electronic cassette 13 so as to communicate in a wired manner or a wireless manner and controls the operation of the electronic cassette 13. Specifically, the console 14 transmits the radiographing conditions to the electronic cassette 13 to set the conditions (such as the gain of the amplifier amplifying the voltage corresponding to the accumulated signal charges) of the signal process of the FPD 35 and to control the turning-on or turning-off of the power source of the electronic cassette 13, the mode switching to a power saving mode or a radiography standby state, and the like.

The console 14 performs various image processes such as offset correction, gain correction, and defect correction on the X-ray image data transmitted from the electronic cassette 13. In the defect correction, the pixel values of the columns having the detection pixel 65 are interpolated with the pixel values of the neighboring columns not having the detection pixel 65. The X-ray image subjected to the image processes is displayed on a display 89 (see FIG. 7) of the console 14. The data thereof is stored in a storage device 87 or a memory 86 (see FIG. 7 for both) in the console 14 or a data storage such as an image storage server connected to the console 14 via a network.

The console 14 receives the input of an examination order including information such as such as gender of a patient, age of a patient, a radiography site, and a radiography purpose and displays the examination order on the display 89. The examination order is input from an external system that manages patient information or examination information relevant to radiographic examinations, such as an HIS (Hospital Information System) or an MS (Radiographic Information System), or is manually input by an operator. The examination order includes radiography sites such as head, chest, and abdomen and radiographing directions such as front, side, oblique, PA (radiation of X-rays from the back of an object), and AP (radiation of X-rays from the front of an object). The operator confirms the details of the examination order through the use of the display 89 and inputs the radiographing conditions corresponding to the details through the use of the operation screen of the console 14.

As shown in FIG. 6, in the console 14, unlike the radiographing conditions of the source controller 11 side having only one radiographing condition for one tube voltage (radiography site), plural more specific radiographing conditions (such as chest PA and chest AP of the tube voltage 120 kV) can be set for one tube voltage (radiography site). An S value is stored for each radiographing condition as a value equivalent to the irradiation-stop threshold value of the radiographing condition of the source controller 11 side. The S value is obtained by analyzing X-ray image data using a histogram and is a representative index value of the dose along with an EI value and an REX value. The information of the radiographing conditions is stored in the storage device 87.

Figure 7:
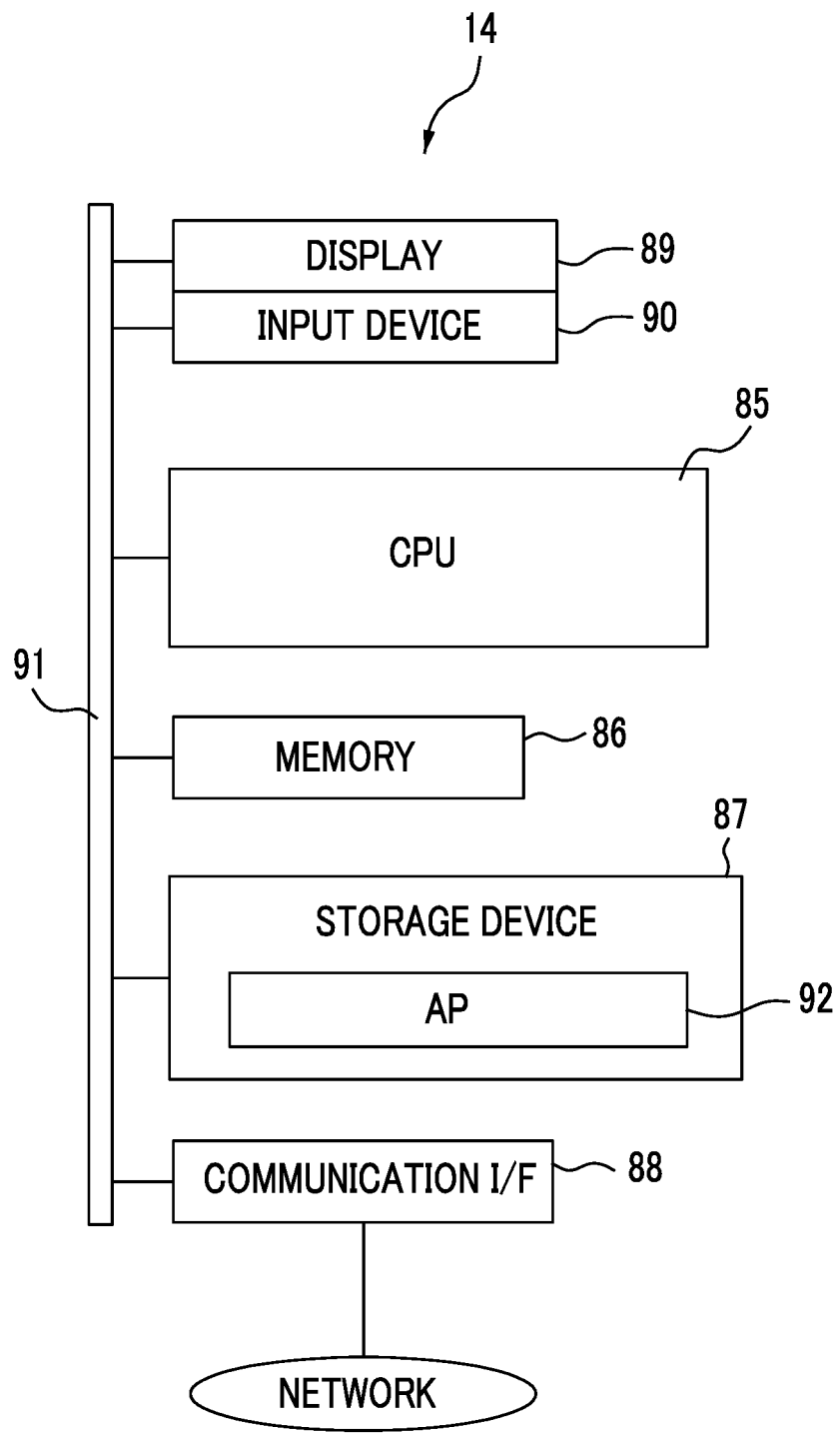
FIG. 7 is a block diagram illustrating the internal constitution of the console.

In FIG. 7, a computer constituting the console 14 includes a CPU 85, a memory 86, a storage device 87, a communication I/F 88, a display 89, and an input device 90. These are connected to each other via a data bus 91.

The storage device 87 is, for example, an HDD (Hard Disk Drive). The storage device 87 stores control programs or application programs (hereinafter, referred to as AP) 92. The AP 92 is a program causing the console 14 to perform various functions relevant to the radiography such as the examination order, the display process of an X-ray image, the image process on the X-ray image, and the setting of the radiographing conditions.

The memory 86 is a work memory in which the CPU 85 performs processes. The CPU 85 loads the control program stored in the storage device 87 into the memory 86 and performs the processes based on the program, thereby generally controlling the units of the computer. The communication I/F 88 is a network interface controlling the transmission to the external apparatuses such as the RIS, the HIS, the image storage server, and the electronic cassette 13. The input device 90 includes a keyboard, a mouse, or a touch panel coupled to the display 89.

Figure 8:
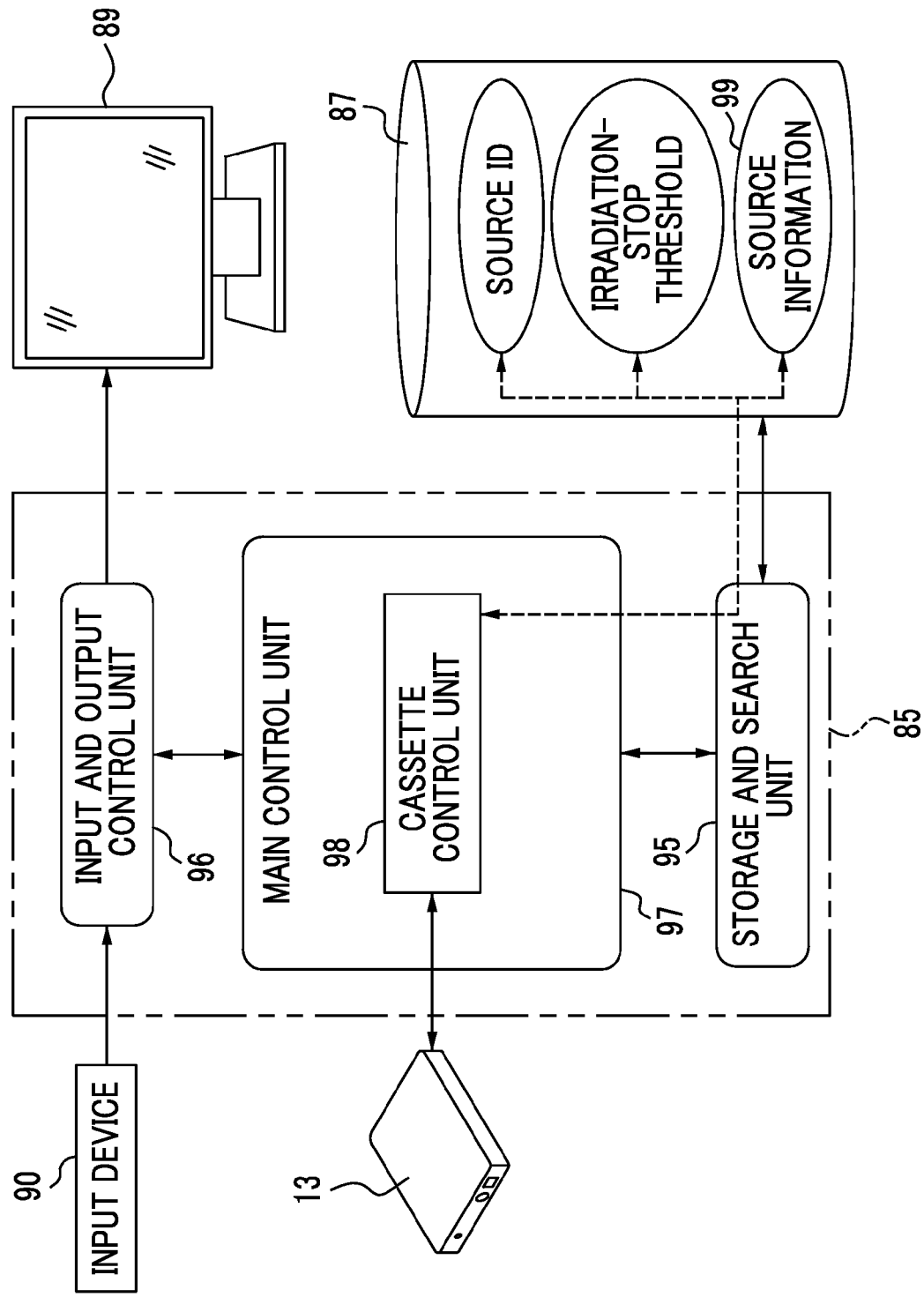
FIG. 8 is a block diagram illustrating the functions of the console and the flow of information.

In FIG. 8, the CPU 85 of the console 14 serves as a storage and search unit 95, an input and output control unit 96, and a main control unit 97, when the AP 92 is started up. The storage and search unit 95 performs a process of storing various data in the storage device 87 and a process of searching for various data stored in the storage device 87. The input and output control unit 96 reads drawing data corresponding to the operation on the input device 90 from the storage device 87 and outputs various operation screens to the display 89 using a GUI based on the read drawing data. The input and output control unit 96 receives the input of an operation instruction from the input device 90 through the use of the operation screen. The main control unit 97 includes a cassette control unit 98 controlling the operation of the electronic cassette 13 and generally controls the operations of the units of the console 14.

The storage device 87 stores source information 99 shown in FIG. 9. The source information 99 stores a regional type of an X-ray source, a radiographing condition, and an AEC specification for each X-ray source ID.

The regional type represents which of installation convenience of the radiographic system and items other than the installation convenience, such as image quality of an X-ray image, should be preferred for each region of domestic, North America, Europe, and Asia. When a new AEC sensor is introduced instead of the old AEC sensor 25 used in the past and the irradiation signal I/F 27 is used instead of the detection signal I/F 26 and when a connection plug of the new AEC sensor for connection to the irradiation signal I/F 27 is selected depending on the specification of the source controller 11 or is newly replaced, a trouble of stopping the function of the detection signal I/F 26 or the like may occur. Such a trouble may cause a case where the installation may not be completed with its high degree of difficulty depending on a serviceman's skill taking charge of the installation. Accordingly, when the installation convenience is preferred, the detection signal I/F 26 is preferably used which is not different from the old AEC sensor 25 used hitherto and of which the result does not depend on the serviceman's skill. If the regional type is set to the installation convenience preference, it means a region in which a serviceman's skill is relatively low or a region in which the image quality of an X-ray image does not matter (see FIG. 10).

On the other hand, as described with reference to FIGS. 2 and 6, the radiographing conditions of the source controller 11 side are limited in numerical values and very fine setting is often not possible. However, when the electronic cassette 13 is introduced, a variety of radiography and the AEC can be used with various radiographic techniques. Accordingly, the radiographing conditions can be more finely set with the console 14. Therefore, compared with the case where the AEC is approximately performed using the irradiation-stop threshold value of the source controller 11 side, there are merits other than the installation convenience, such as the improvement in image quality of an X-ray image, in a case where the electronic cassette 13 side performs the AEC on the basis of the irradiation-stop threshold values corresponding to the fine radiographing conditions, specifically, the electronic cassette 13 side determines the irradiation stop with X-rays using the threshold values corresponding to the fine radiographing conditions and transmits and receives the irradiation stop signal via the irradiation signal I/F 27 and 81. The region in the regional type in which the installation convenience non-preference is set is a region in which a serviceman's skill causes no problem or a region in which the merits other than the installation convenience, such as the image quality of an X-ray image, is preferred instead of the installation convenience (see FIG. 10).

The radiographing conditions of the source information 99 include the same as stored in the source controller of each X-ray source, except for the irradiation-stop threshold values which can be adjusted by an operator. The AEC specification includes an item on which of the value of each detection field, the sum of the detection fields, and the average value thereof should be output (not shown) in addition to the presence of the integration circuit integrating the AEC detection signal and the positions of the detection fields (xy coordinates of two points diagonally connected when the detection field has a rectangular shape) expressed by xy coordinates. The xy coordinates of the detection fields correspond to the positions of the pixels 45 (including the detection pixels 65) in the imaging plane 36 of the electronic cassette 13, and the coordinates of the upper-left pixel 45 are expressed as an origin (0, 0) with the direction parallel to the scanning lines 51 as an x axis and the direction parallel to the signal lines 52 as a y axis. Here, the type information is acquired by information acquiring part of the CPU 85 and is stored in the source information 99 of the storage device 87. A part of the source information 99 in the console 14 corresponds to the first storage part.

The source information 99 also stores correction information. The correction information represents the correlation between the new AEC detection signal and the old AEC detection signal of each X-ray source for each tube voltage and is stored in the form of a data table or a function. Here, a part of the source information 99 corresponds to the second storage part.

Since the old AEC sensor 25 is used in a state where it is placed on the front surface of the imaging plane of the cassette, the amount of X-rays incident on the imaging plane of the cassette from the X-ray source is reduced by the old AEC sensor 25 itself. In this case, the irradiation-stop threshold value of the old AEC sensor 25 is set to a value obtained by adding the dose absorbed by the old AEC sensor to the dose necessary for the image quality. On the other hand, since the detection pixels 65 are used as a new AEC sensor in the electronic cassette 13, an intermediate member such as the housing of the electronic cassette 13 is disposed between the X-ray source and the electronic cassette. When the electronic cassette 13 is of the PSS type in which the scintillator and the FPD 35 are arranged in this order as viewed from the incidence side of X-rays, the scintillator is also an intermediate member (on the contrary, the scintillator is not an intermediate member in the ISS type). The same is true when a grid for removing X-rays scattered in an object is disposed between the X-ray source 10 and the electronic cassette 13 with the introduction of the electronic cassette 13. When the detection pixels 65 of the electronic cassette 13 are used instead of the old AEC sensor 25, an output value may be lowered, for example, to "0.8" in the new AEC detection signal due to the interposition of the intermediate member at the dose with which the value of "1" is output in the old AEC detection signal.

The range formats of the old AEC detection signal and the new AEC detection signal may be different from each other, such as when the old AEC detection signal is expressed with the minimum of −5 V and the maximum of 5 V but the new AEC detection signal is expressed with the minimum of 0 mV and the maximum of 5 mV. Accordingly, it is necessary to know which of the old AEC sensor and the new AEC sensor should be used or which value the new AEC detection signal has in the old AEC detection signal by dissolving the difference between the old AEC detection signal and the new AEC detection signal due to the presence or absence of the intermediate member or the difference in range format. The correction information is information used to surely know which value the new AEC detection signal has in the old AEC detection signal and to dissolve the difference between the old AEC detection signal and the new AEC detection signal. The correction information is obtained through comparison of the configurations (such as the PSS type or the ISS type, the presence or absence of scintillator, materials when the scintillator is present, the presence or absence of the grid, and materials when the grid is present) of the device such as the old AEC sensor 25 used hitherto and the device such as the electronic cassette 13 to be used from now on and preliminary experiments or simulations. The presence or absence of the scintillator is acquired from the specification information of the electronic cassette 13 indicating the PSS type or the ISS type. The presence or absence of the grid is selected by displaying a GUI on the display 89 of the console 14. Here, since the X-ray detection principles as well as the intermediate member are different between the old AEC sensor and the new AEC sensor, the detected doses are different for the same incident dose. The difference in detected dose due to the difference in detection principle is dissolved through the experiment or simulation.

Regarding the source information 99, the latest information is supplied via a network or the like and the source information is frequently updated, when a new product of an X-ray source is released. Alternatively, instead of automatically updating the source information, the information of an X-ray source which can be used in the system may be received from the manufacturer thereof and may be manually input through the use of the input device 90.

Figure 11:
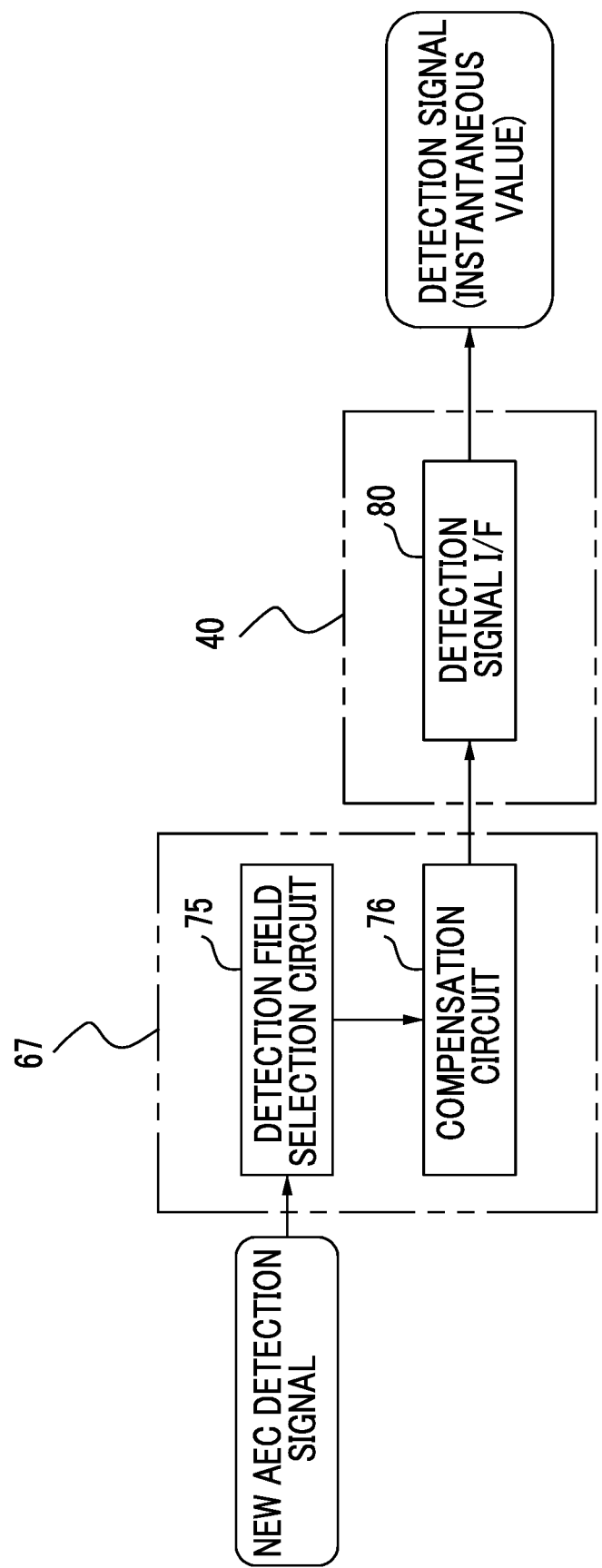
FIG. 11 is a diagram illustrating operating situations of the communication unit and the AEC unit when the regional type is installation convenience preference and an integration circuit is disposed in the source controller.
Figure 12:
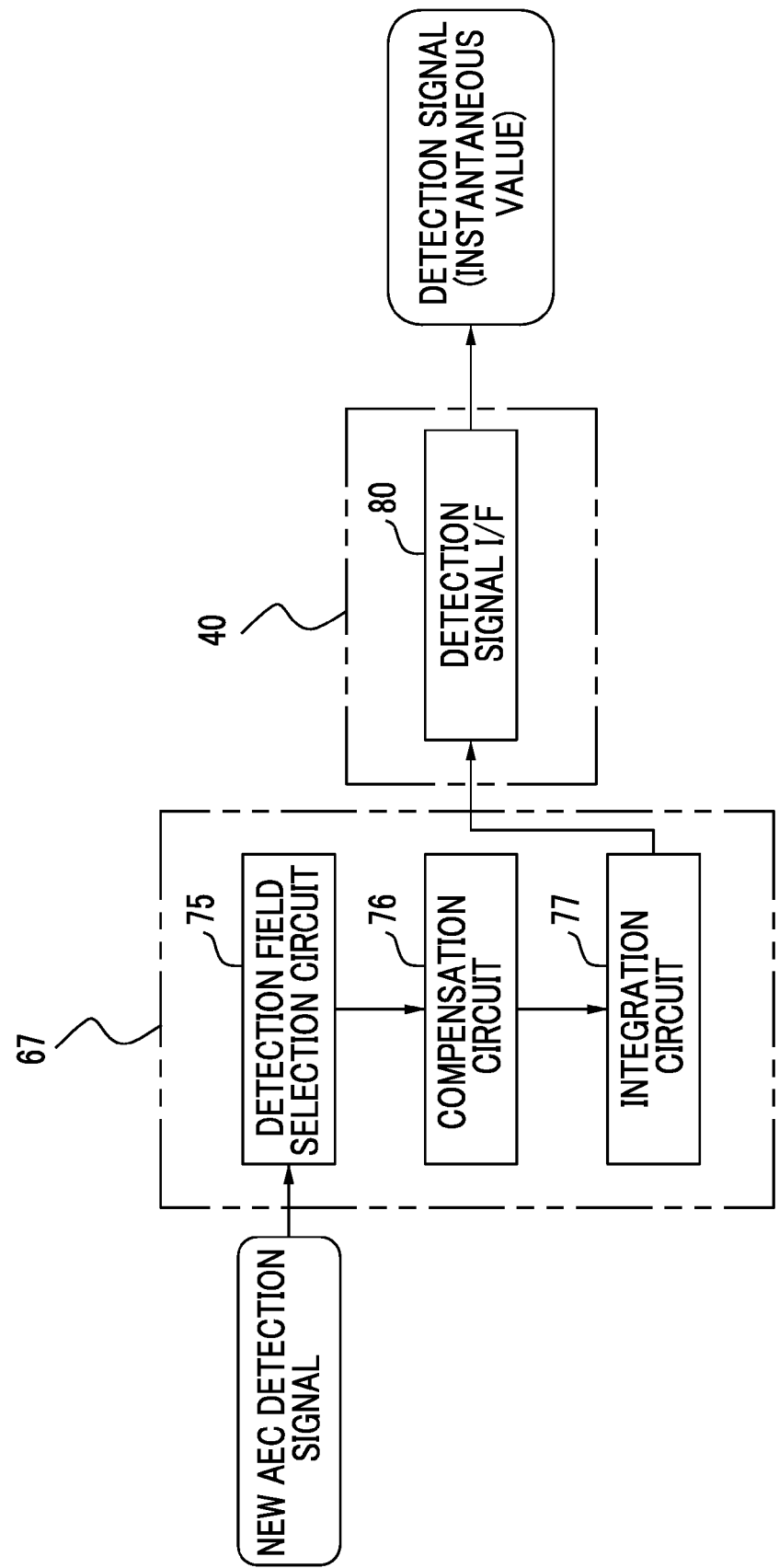
FIG. 12 is a diagram illustrating operating situations of the communication unit and the AEC unit when the regional type is installation convenience preference and an integration circuit is not disposed in the source controller.

Here, an example of the radiographic system 2 where the cassette and the console used hitherto are replaced with the electronic cassette 13 and the console 14 and the detection pixels 65 of the electronic cassette 13 are newly used as the AEC sensor instead of the old AEC sensor 25 disposed in the X-ray source 10 will be described with reference to the table shown in FIG. 10, the diagrams illustrating the operating situations of the communication unit 40 and the AEC unit 67 in FIGS. 11 to 13, and the flowcharts shown in FIGS. 14 and 15.

Figure 14:
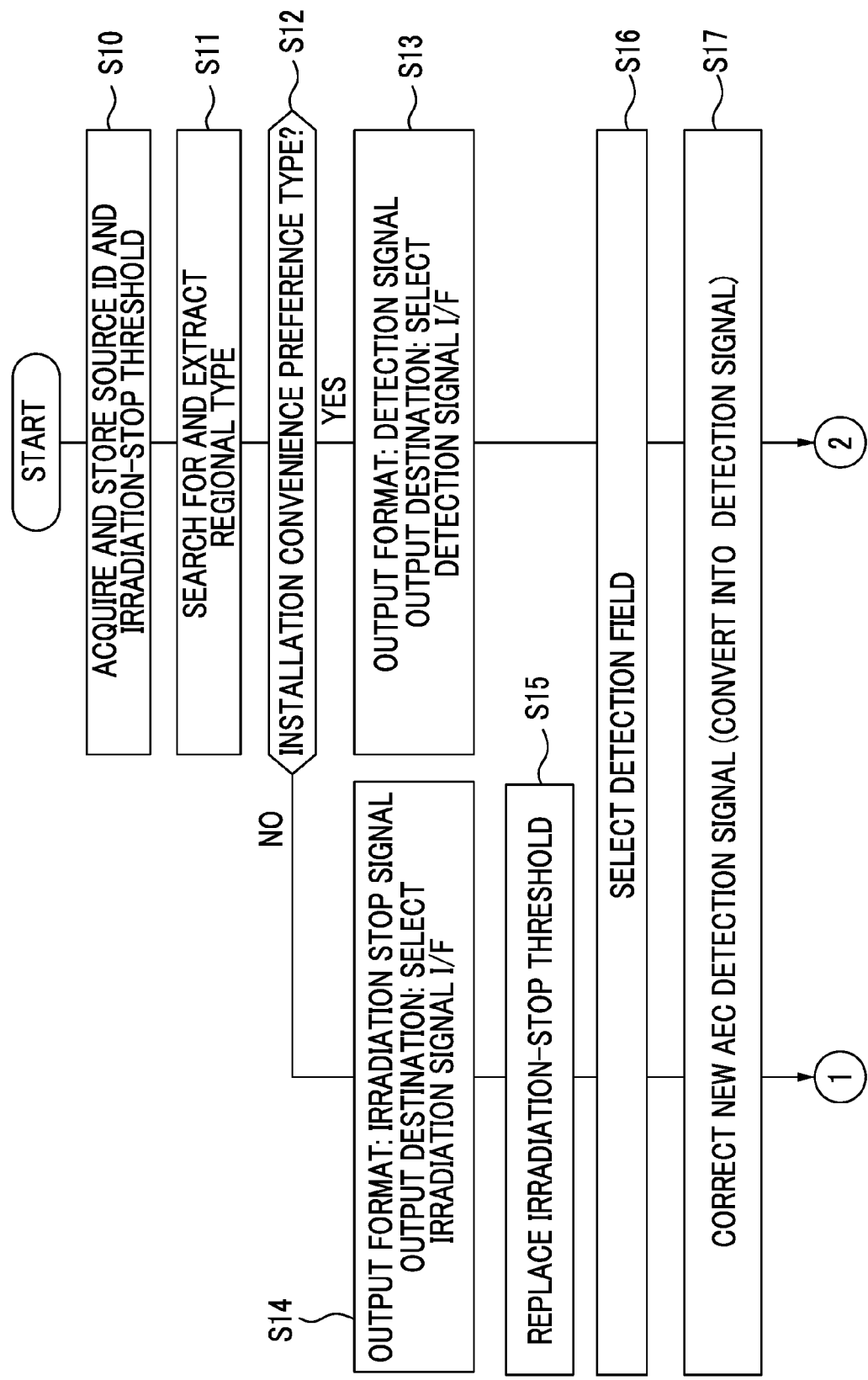
FIG. 14 is a flowchart illustrating the flow of operations of the communication unit and the AEC unit.
Figure 15:
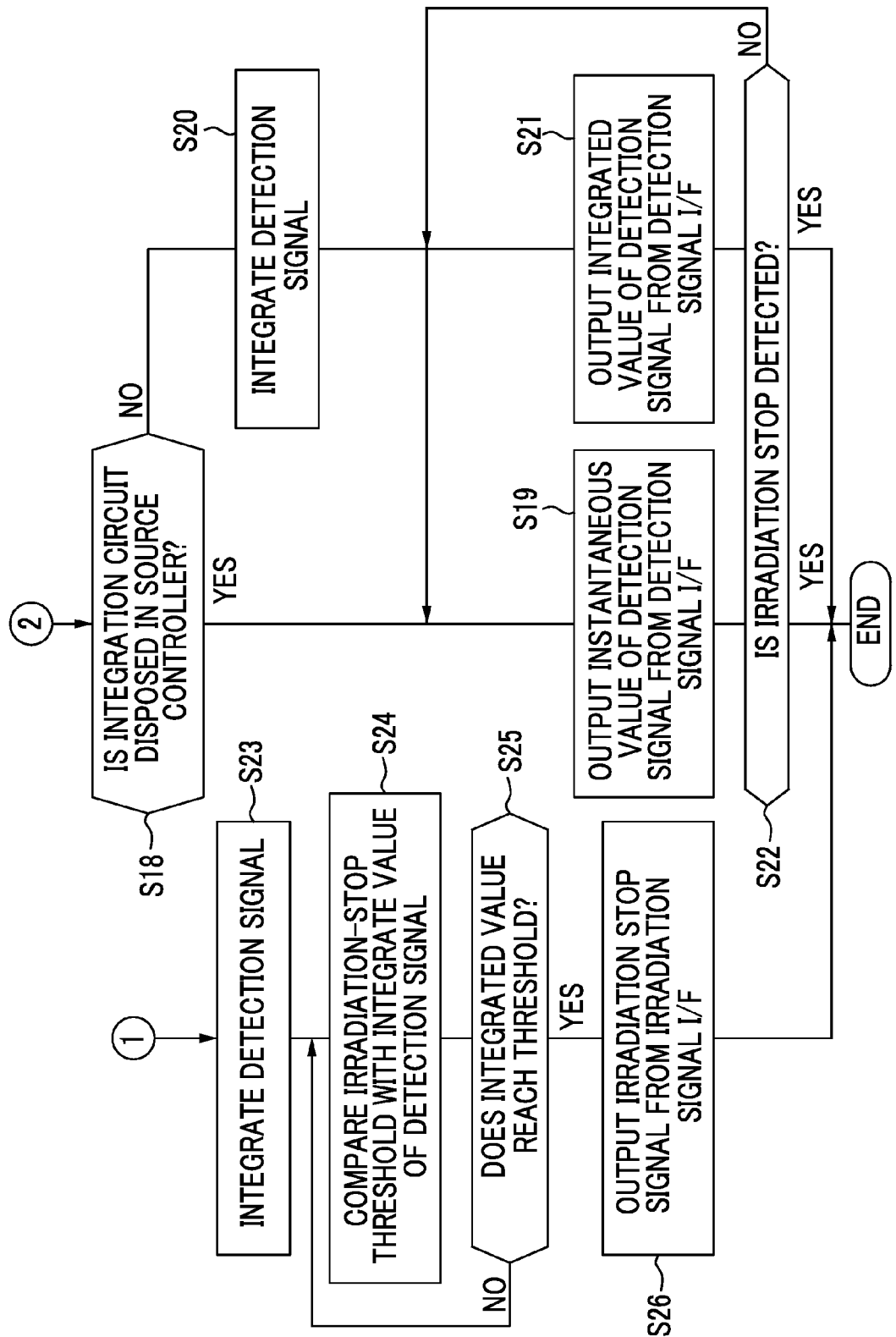
FIG. 15 is a flowchart illustrating the flow of operations of the communication unit and the AEC unit.

As shown in step 10 (S10) of FIG. 14, the storage and search unit 95 sets up communication with the source controller 11 and stores information such as a source ID and an irradiation-stop threshold value transmitted from the communication I/F 22 of the source controller 11 in the storage device 87 (see FIG. 8). The storage and search unit 95 searches for and extracts the source ID received from the source controller 11 and a regional type set in advance at the time of shipment from the item of regional type in the source information 99 (S11). The radiographing condition, the AEC specification, and the correction information corresponding to the source ID are extracted from the source information 99. The information extracted by the storage and search unit 95 can be sent from the cassette control unit 98 to the electronic cassette 13 along with the information of the irradiation-stop threshold value.

Selection of Output Destination and Output Format

The control unit 41 of the electronic cassette 13 selects the output destination and the output format of the AEC signal on the basis of the information of the regional type given from the console 14. Specifically, as shown in FIG. 10, when the regional type is the installation convenience preference (YES in S12), the output destination of the communication unit 40 is set to the detection signal I/F 80 and the output format is set to the detection signal (S13). When the regional type is the installation convenience non-preference (NO in S12), the output destination is set to the irradiation signal I/F 81 and the output format is set to the irradiation stop signal (S14). In the former, the more output format is selected on the basis of the presence or absence of an integration circuit in the AEC specification and the information on which of the values of the detection fields, the sum of the detection fields, and the average value of the detection fields should be output. Here, the switching part for selectively switching the output format is included in the control unit 41 of the electronic cassette 13.

Positioning of Detection field

The detection field selecting circuit 75 selects new AEC detection signals from the detection pixels 65 present at the positions of the detection fields of the old AEC sensor 25 out of the new AEC detection signals of the plural detection pixels 65 input from the A/D converter 62 on the basis of the information of the positions of the detection fields of the old AEC sensor 25 given from the console 14, and outputs the selected new AEC detection signal to the correction circuit 76 (S16). In the case of the source ID "0001" in this example, the new AEC detection signals of the detection pixels 65 present in the range of a' to c' shown in FIG. 4 and corresponding to the detection fields a to c are selected by the detection field selecting circuit 75.

Positioning of Detection fields in Consideration of Posture of Cassette

There are some radiography platforms on which an electronic cassette can be mounted with the posture of the electronic cassette changed by 90° such as vertical setting and horizontal setting. An example is considered where such a radiography platform is used. In this case, when the information of the positions of the detection fields of the old AEC sensor 25 is employed without any change as in the above-mentioned embodiment and the detection field is selected by the detection field selecting circuit 75, the detection field may be selected at a different position depending on the posture of the electronic cassette. In order to prevent this situation, for example, as described in JP2011-067314A, it is preferable that the mounting posture of the electronic cassette on the radiography platform be detected using a photo sensor and the detection field be selected by the detection field selecting circuit 75 on the basis of the information of the detection result.

More specifically, when the positional information of the detection field in the old AEC sensor 25 indicates the vertical setting and the mounting posture of the electronic cassette is the horizontal setting, the positional information (coordinates) of the detection field in the old AEC sensor 25 is rotated by 90° or 270° about the center of the imaging plane of the cassette. Alternatively, the positional information of the detection field of the old AEC sensor 25 corresponding to the vertical setting and the horizontal setting is stored in advance as the source information 99 and the information to be used may be selected on the basis of the detection result of the mounting posture of the cassette.

Correction of Detection Signal

The correction circuit 76 converts the new AEC detection signal input from the detection field selecting circuit 75 into a detection signal on the basis of the correction information suitable for the radiographing condition (tube voltage) at that time (S17). The correction circuit 76 performs operations such as summing or averaging on the detection signal if necessary on the basis of the information on which of the values of the detection fields, the sum of the detection fields, and the average of the detection fields should be output. The selection of the detection field and the correction should be necessarily performed regardless of the regional type (see FIG. 10).

When it is determined that the regional type is the installation convenience preference and the source controller 11 includes an integration circuit on the basis of the information on the presence or absence of the integration circuit in the AEC specification (YES in S18 of FIG. 15), the detection signal itself (instantaneous value) output from the correction circuit 76 is transmitted to the detection signal I/F 26 of the source controller 11 via the detection signal I/F 80 at a predetermined transmission interval (S19). In this case, in the AEC unit 67, only the detection field selecting circuit 75 and the correction circuit 76 are activated as shown in FIG. 11.

On the other hand, when the regional type is the installation convenience preference and the source controller 11 does not include an integration circuit (NO in S18), the correction circuit 76 outputs a detection signal to the integration signal 77 and the integration circuit 77 integrates the detection signal (S20). The integrated value of the detection signal from the integration circuit 77 is transmitted to the detection signal I/F 26 of the source controller 11 via the detection signal I/F 80 at a constant transmission interval (S21). The instantaneous value or the integrated value of the detection signal is continuously transmitted until the irradiation stop with X-rays is detected (YES in S22). As shown in FIG. 12, in the AEC unit 67, the detection field selecting circuit 75, the correction circuit 76, and the integration circuit 77 are activated.

When the regional type is the installation convenience preference, the instantaneous value or the integrated value of the detection signal is transmitted from the electronic cassette 13 to the source controller 11. The determination of the irradiation stop with X-rays is performed by the source controller 11 side to which the instantaneous value or the integrated value of the detection signal is transmitted. Similarly to the case where the old AEC sensor 25 is used, the irradiation stop with X-rays is determined through comparison of the integrated value of the detection signal with the irradiation-stop threshold value. Accordingly, the information of the irradiation-stop threshold value of the source controller 11 side when the regional type is the installation convenience preference is not necessary and the replacement of a threshold value to be described later when the regional type is the installation convenience non-preference is also not necessary (see FIG. 10).

Figure 13:
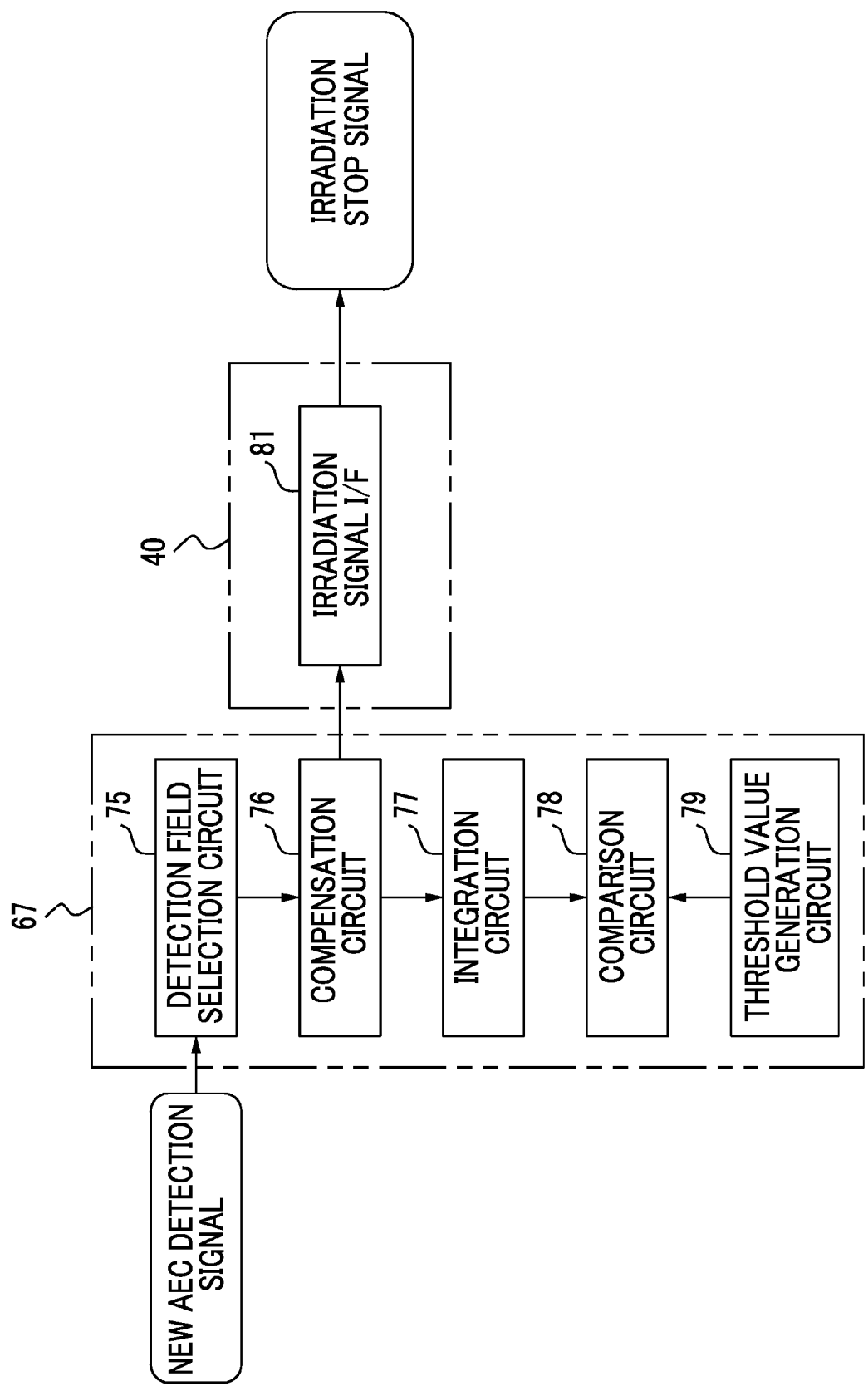
FIG. 13 is a diagram illustrating operating situations of the communication unit and the AEC unit when the regional type is installation convenience non-preference.

When the regional type is the installation convenience non-preference, the comparison circuit 78 and the threshold generating circuit 79 are further activated, as shown in FIG. 13. First, similarly to the case where the regional type is the installation convenience preference and the source controller 11 does not include an integration circuit, the correction circuit 76 outputs the detection signal to the integration circuit 77 and the integration circuit 77 integrates the detection signal (S23).

Replacement of Threshold Value

The threshold generating circuit 79 replaces the S value set as the irradiation-stop threshold value of the radiographing conditions of the console 14 side with the irradiation-stop threshold value of the radiographing conditions of the source controller 11 side (S15 in FIG. 14). Here, since only one radiographing condition of the source controller 11 side is set for one tube voltage (radiography site) and the same is true of the irradiation-stop threshold value, this cannot be applied to the plural S values of the console 14 side which are set for one tube voltage (radiography site). Accordingly, the S value of a representative radiographing condition (for example, chest PA) among plural radiographing conditions of the console 14 side is replaced with the irradiation-stop threshold value of the radiographing condition of the source controller 11. The S value is replaced with an adjusted value when the irradiation-stop threshold value is the adjusted value, the S value is replaced with a default value when the irradiation-stop threshold value is the default value.

Regarding other radiographing conditions other than the representative radiographing condition, the original S values including the representative radiographing condition are converted into doses, the converted doses are converted into the irradiation-stop threshold values, the ratios to the irradiation-stop threshold value of the representative radiographing condition is calculated, and the irradiation-stop threshold values are calculated by multiplying the ratios by the replaced irradiation-stop threshold value. For example, when the replaced irradiation-stop threshold value of the chest PA at the tube voltage 120 kV of the representative radiographing condition is 6, the irradiation-stop threshold value into which the original S value is converted is 5, and the irradiation-stop threshold value into which the original S value of the chest AP is converted is 4 at the same tube voltage 120 kV, 6×(4/5)=4.8 is the irradiation-stop threshold value of the radiographing condition of the chest AP. The threshold generating circuit 79 outputs the irradiation-stop threshold value replaced for the radiographing condition of the source controller 11 side to the comparison circuit 78 in accordance with the radiographing condition set by the console 14 side.

The comparison circuit 78 compares the irradiation-stop threshold value from the threshold generating circuit 79 with the integrated value of the detection signal from the integration circuit 77 (S24 in FIG. 15) and outputs the irradiation stop signal when the integrated value reaches the threshold value (YES in S25). The irradiation stop signal output from the comparison circuit 78 is transmitted to the irradiation signal I/F 27 of the source controller 11 via the irradiation signal I/F 27 (S26).

When the regional type is the installation convenience non-preference, the new AEC detection signal from the detection pixels 65 is converted into the detection signal corresponding to the old AEC detection signal by the correction circuit 76 and this detection signal is compared with the irradiation-stop threshold value replaced for the radiographing condition of the source controller 11, whereby the irradiation stop with X-rays is determined. That is, the same control as the AEC performed by the control unit 21 of the source controller 11 using the old AEC sensor 25 is performed by the electronic cassette 13. Here, since the irradiation-stop threshold value is changed depending on the plural radiographing conditions, it is possible to perform the more precise AEC than the AEC performed by the source controller 11.

As described above, according to the present invention, since the output destination and the output format of the AEC signal is selected depending on the regional type of the installation convenience preference or the installation convenience non-preference, it is possible to flexibly cope with the situations of the place in which the radiographic system 2 is installed.

Since the irradiation-stop threshold value of the source controller 11 side is not corrected and maintained in the old state and the irradiation stop with X-rays is determined after the new AEC detection signal is corrected to a value corresponding to the old AEC detection signal by the electronic cassette 13 side, it is possible to use the electronic cassette 13 having the detection pixels 65 as the new AEC sensor without changing the setting of the source controller 11 side without hindrance. Since the manufacturer of the X-ray generator and the manufacturer of the X-ray imaging apparatus may be different from each other, a serviceman of the source manufacturer should be called to correct the irradiation-stop threshold value of the source controller 11 side, which is very troublesome. However, in the present invention, since the correction is completed by only the electronic cassette 13 side, such a trouble is not caused, which can be used as a sales point for introduction of a new system. It is possible to succeed to tendencies of operators or polishes of hospitals of lowering the dose to reduce exposure of a patient to radioactivity or raising the dose to slightly raise the concentration of an X-ray image without changing the old states.

Since the detection pixel 65 is selected by the detection field selecting circuit 75 so as to obtain the same detection field as in the old AEC sensor 25, it is possible to perform the AEC not different from the old state.

The present invention is not limited to the above-mentioned embodiment, but may employ various forms without departing from the concept of the present invention.

Figure 16:
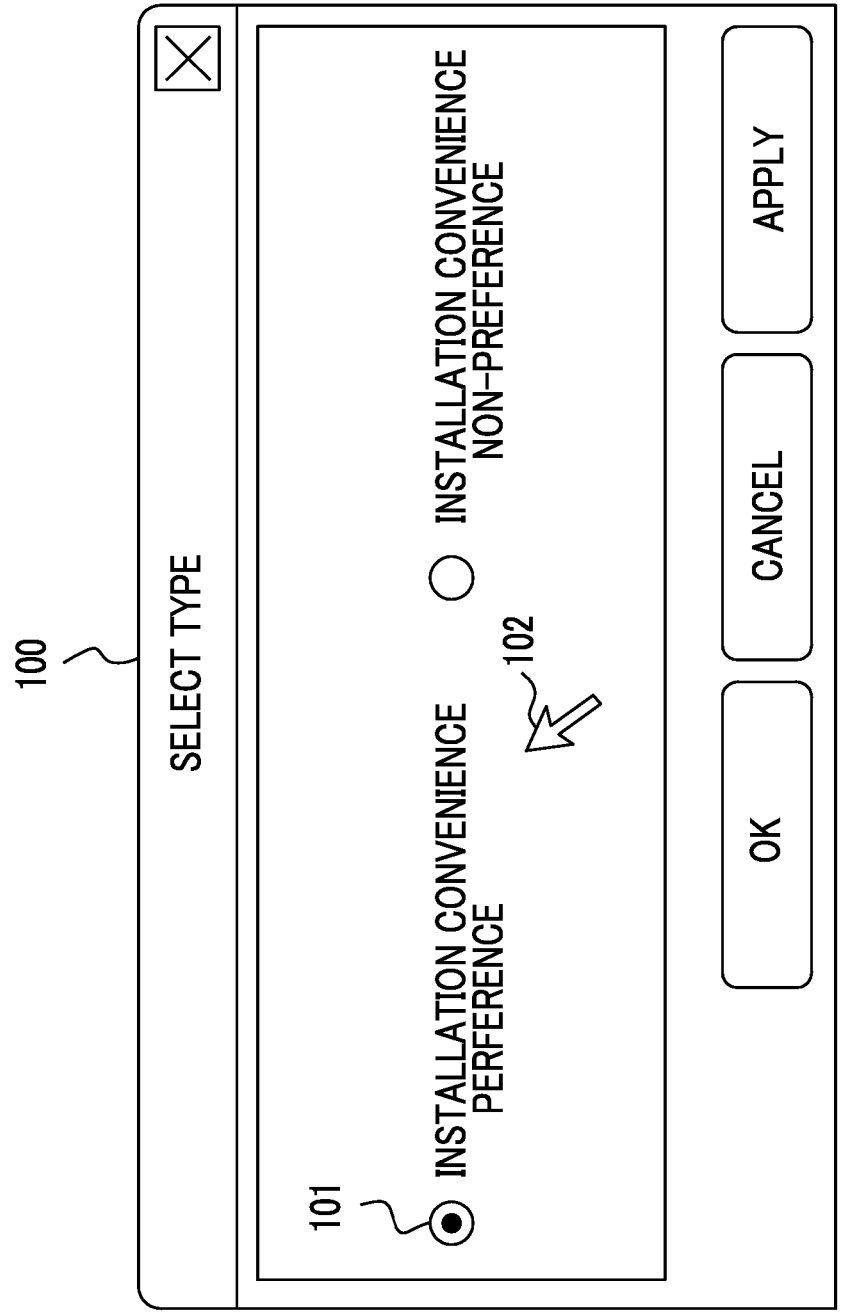
FIG. 16 is a diagram illustrating an example of a type selection window for manually inputting a regional type.

In the above-mentioned embodiment, when the communication between the source controller 11 and the console 14 is set up after the installation is finished, the source ID is exchanged and the regional type of the X-ray source 10 having the source ID is searched for and extracted from the source information 99, but the regional type may be manually input by an operator. In this case, a type selection window 100 shown in FIG. 16 is displayed on the display 89 of the console 14 or on the display unit (not shown) of the electronic cassette 13. The type selection window 100 includes a radio button 101 for alternatively selecting the installation convenience preference type and the installation convenience non-preference type. An operator can select the type by allowing the operator to click the radio button 101 with a pointer 102 through the input device 90 or the operation unit (not shown) of the electronic cassette 13. Similarly, the source ID may be manually input by an operator without being automatically acquired.

The installation convenience preference type and the installation convenience non-preference type are stored as set values in the electronic cassette 13 and any one may be set at the time of shipment by the manufacturer side of the electronic cassette 13 or an agency of the manufacturer in advance. The electronic cassette 13 changes its operation depending on the set type. Accordingly, it is possible to save the labor of a hospital side as a client for selecting the type. It is also possible to save the labor of the manufacturer for preparing for software controlling the electronic cassette 13 for each type or selecting and installing software produced differently depending on the regions and thus to improve the productivity.

Use of Converter

Figure 17:
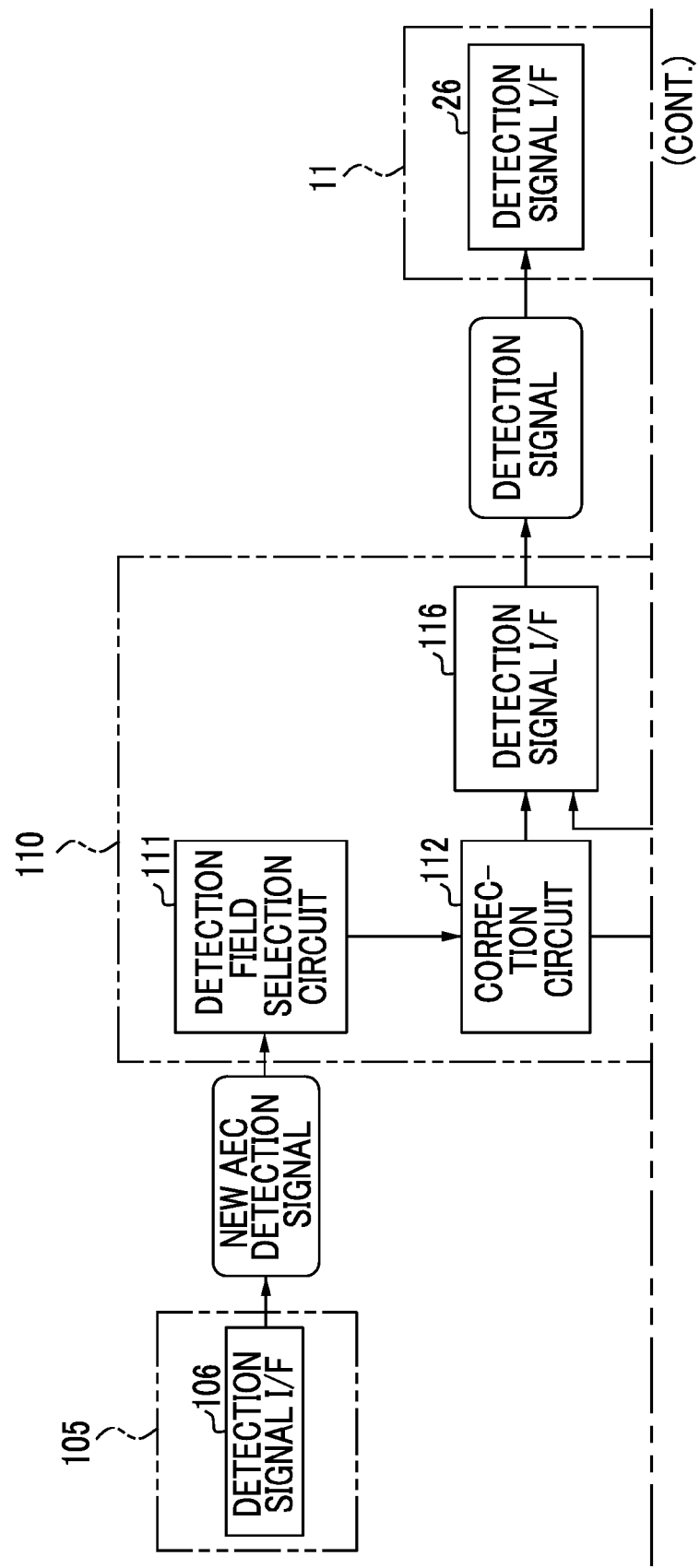
FIG. 17 is a block diagram illustrating an example where a converter is provided.

In the above-mentioned embodiment, the electronic cassette 13 including both the detection signal I/F 80 and the irradiation signal I/F 81 selects what I/F to use depending on the regional type of the X-ray source 10. However, as shown in FIG. 17, only the detection signal I/F 106 which is standard equipment may be disposed in an electronic cassette 105, the new AEC detection signal may be output from the detection signal I/F 106, a converter 110 having the functions of the AEC unit 67 and the communication unit 40 shown in FIG. 5 may be disposed between the electronic cassette 105 and the source controller 11, and the output destination and the output format may be selected by the converter 110.

In this case, the converter 110 is connected to the console 14 and receives the regional type, the radiographing conditions, the AEC specification, the correction information, and the irradiation-stop threshold value of the source information 99 from the console 14. The units of the converter 110 such as both a detection signal I/F 116 and an irradiation signal I/F 117 in addition to a detection field selecting circuit 111 are referenced by different reference numerals but have the same functions as the AEC unit 67 and the communication unit 40 shown in FIG. 5. The converter 110 determines the output destination and the output format depending on the regional type transmitted from the console 14 and maintains the state as long as the X-ray source 10 is not replaced.

Since the functions of the AEC units 67 and the like are transplanted into the converter 110, it is possible to promote a decrease in size and a decrease in weight of the electronic cassette 105. When the electronic cassette 105 is shared by plural radiography rooms in a hospital having the radiography rooms and the regional types of the X-ray sources 10 of the radiography rooms are different from each other, it is necessary to change the output destination and the output format in the electronic cassette 13 according to the above-mentioned embodiment. However, by disposing the converter 110 between the source controller 11 and the electronic cassette 105, it is possible to save the labor of the electronic cassette side for switching the output destination and the output format.

AEC using Detection Signal I/F

Figure 18:
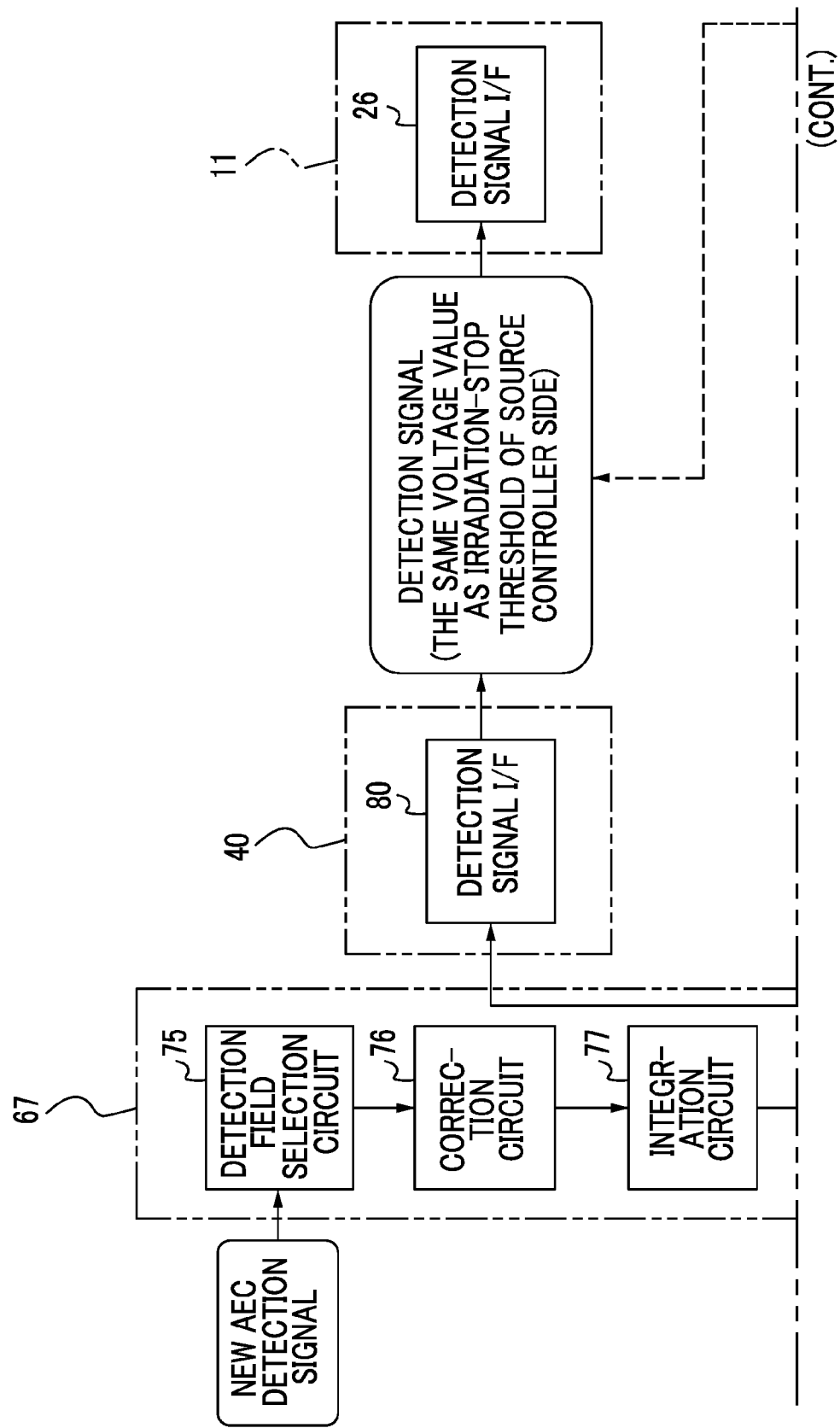
FIG. 18 is a diagram illustrating a coping technique when a radiographing condition and an irradiation-stop threshold which can be set by the source controller side are smaller than those which can be set by the electronic cassette side.

When the regional type is the installation convenience preference type, the output destination is set to the detection signal I/F, the output format is set to the value (detection signal), and the determination of the irradiation stop is performed by the source controller 11 side in which the number of radiographing conditions (irradiation-stop threshold values) is limited. Accordingly, the image quality of an X-ray image is slightly lower than that when the electronic cassette 13 performs the AEC on the basis of the irradiation-stop threshold value based on the fine radiographing conditions. Therefore, when the number of radiographing conditions of the source controller 11 side is smaller than that of the electronic cassette 13 side, it is possible to perform the AEC on the basis of the irradiation-stop threshold value based on the fine radiographing conditions while using the detection signal I/F, by employing the configuration shown in FIG. 18.

First, until the detection field is selected and the irradiation stop is determined, the same processes as in the case where the regional type is the installation convenience preference in the above-mentioned embodiment are performed. Here, the detection signal I/F 80 instead of the irradiation signal I/F 81 is used as an I/F. In addition, when the integrated value of the detection signal reaches the irradiation-stop threshold value from the threshold generating circuit 79, the irradiation stop signal is not output from the irradiation signal I/F 81 but the same voltage value as the irradiation-stop threshold value (such as th1' and th2 in FIG. 2) of the source controller 11 side at the tube voltage is transmitted from the detection signal I/F.

The irradiation-stop threshold value from the threshold generating circuit 79 has various values at the same tube voltage depending on the radiographing conditions set by the console 14 side (see FIG. 6). Since the determination of the irradiation stop with X-rays is performed on the basis of the threshold value corresponding to the radiographing conditions, the time varies depending on the radiographing conditions. However, according to this method, the signal transmitted from the electronic cassette 13 to the source controller 11 is only the same voltage value (one kind in this example) as the irradiation-stop threshold value of the source controller 11 side. That is, the same voltage value as the irradiation-stop threshold value of the source controller 11 side plays a role of the irradiation stop signal and the detection signal I/F 26 and the detection signal I/F 80 can be said to be an I/F dedicated to transmission and reception of the irradiation stop signal. The determination of the irradiation stop is actually performed by the electronic cassette 13, but it seems that the source controller 11 determines the irradiation stop by itself by receiving the same voltage value as the irradiation-stop threshold value.

It is possible to achieve both the merit of installation convenience due to the use of the detection signal I/F 80 and the merit of an increase in image quality due to the use of the irradiation signal I/F 81. This type may be inserted as a compatible type of installation convenience and image quality into the regional type of the above-mentioned embodiment. When the radiographing conditions of the source controller 11 are two or more kinds at the same tube voltage, the radiographing conditions of the console 14 side may be classified into groups in advance, each group may be correlated with one radiographing condition at the same tube voltage of the source controller 11, and the same voltage value as the irradiation-stop threshold value of the radiographing condition of the source controller 11 side is transmitted.

Speed-Up of AEC

As described in the above-mentioned embodiment, the irradiation signal I/F 27 of the source controller 11 exchanges other irradiation signals such as an inquiry signal and an irradiation permission signal in addition to the irradiation stop signal with the irradiation signal I/F 81 of the electronic cassette 13. Accordingly, a branching process of determining what signal is received and determining what to do on the basis of the determination result is necessary and thus the rapidity is insufficient. Different types of signals may be received at the same time and thus the AEC, particularly, the process of stopping the irradiation with X-rays, may be delayed. For example, the irradiation time in radiographing a chest is 50 ms which is very short and thus the process of stopping the irradiation with X-rays should be performed rapidly.

Figure 19:
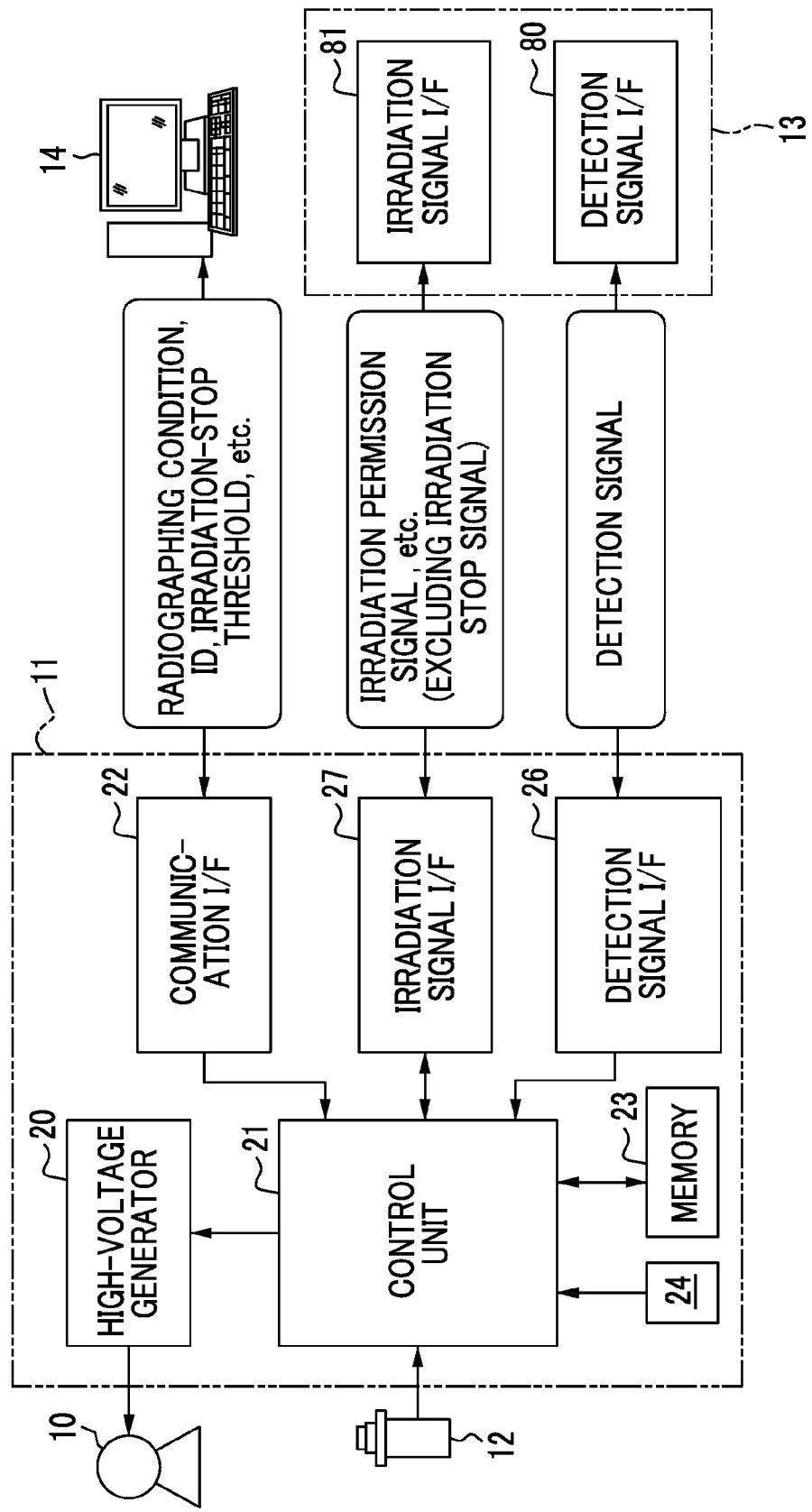
FIG. 19 is a block diagram illustrating an example where a signal other than an irradiation stop signal is exchanged with an irradiation signal I/F and a detection signal is exchanged with a detection signal I/F.

Therefore, as shown in FIG. 19, the detection signal I/F 26 of the source controller 11 and the detection signal I/F 80 of the electronic cassette 13 are connected to each other, the irradiation signal I/F 27 of the source controller 11 and the irradiation signal I/F 81 of the electronic cassette 13 are connected to each other, other signals other than the irradiation stop signal are exchanged between the irradiation signal I/F 27 and 81, and the detection signal is exchanged between the detection signal I/F 26 and 80. That is, the same processes as in the installation convenience preference type in the above-mentioned embodiment are preformed for the exchange of the detection signal and the same processes as in the installation convenience non-preference type are performed for the other irradiation permission signal and the like.

Figure 20:
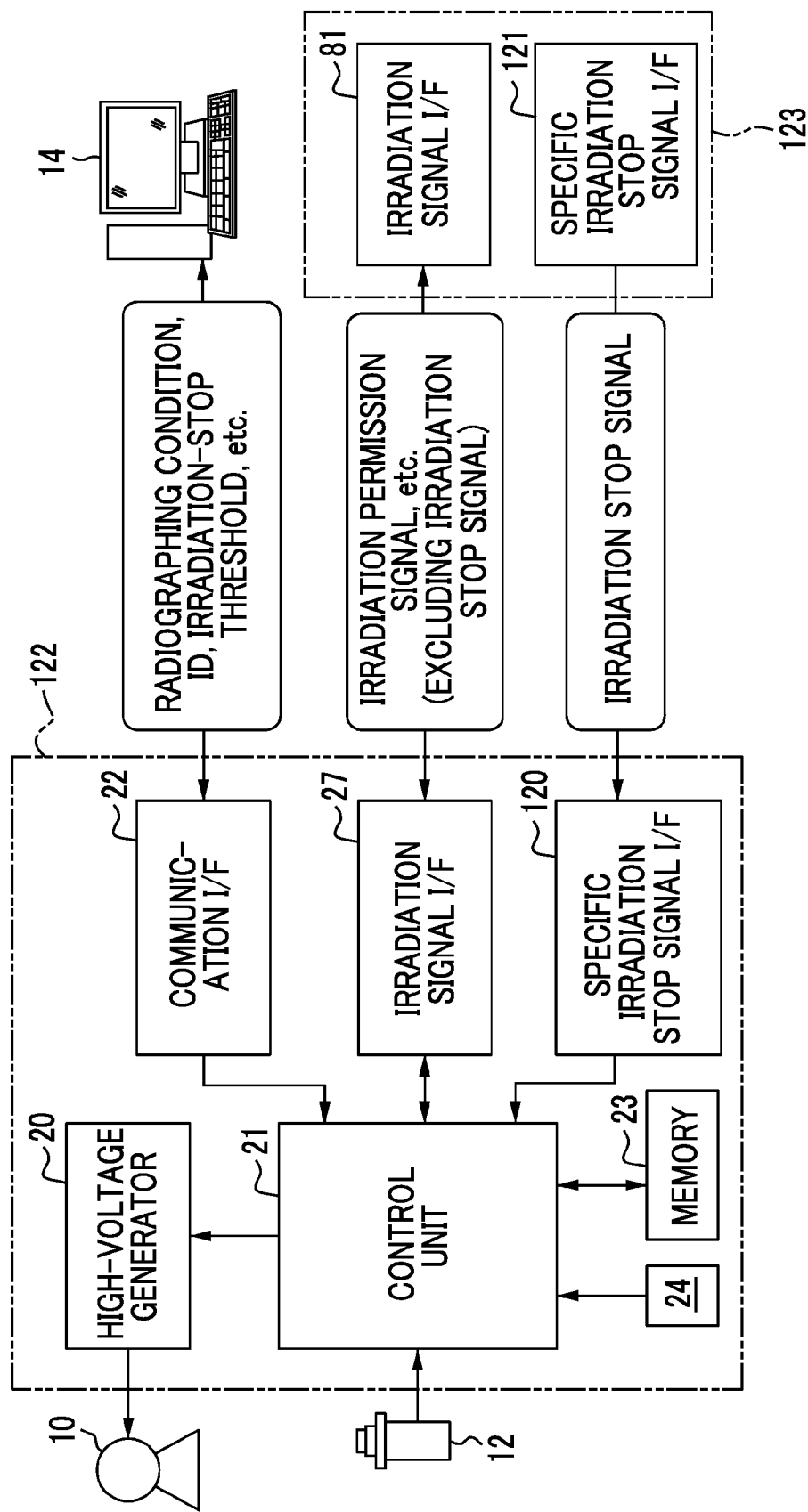
FIG. 20 is a block diagram illustrating an example where a signal other than an irradiation stop signal is exchanged with an irradiation signal I/F and the irradiation stop signal is exchanged with a specific irradiation stop signal I/F.

Alternatively, as shown in FIG. 20, a source controller 122 and an electronic cassette 123 including dedicated irradiation stop signal I/F 120 and 121 disposed independently of the irradiation signal I/F 27 and 81 so as to exchange only the irradiation stop signal may be employed. In this case, the same processes as in the installation convenience non-preference type of the above-mentioned embodiment are performed, but the transmission and reception of the irradiation stop signal is performed by the dedicated irradiation stop signal I/F 120 and 121 instead of the irradiation signal I/F 27 and 81. In this way, when the detection signal associated with the determination of the irradiation stop with X-rays or the irradiation stop signal is exchanged through the use of dedicated I/F other than the I/F exchanging the other signals, it is not necessary to perform the branching process of determining the type of a signal and determining the process based on the determination result and different types of signals are not received at the same time, thereby rapidly performing the process of stopping the irradiation with X-rays.

By causing the other signals not to be transmitted from the electronic cassette when transmitting and receiving the irradiation stop signal between the source controller and the electronic cassette, the source controller side can be prevented from receiving different types of signals at the same time. However, in this method, there is a problem in that the signal transmission control of the electronic cassette side is complicated. In this embodiment, since the detection signal associated with the determination of the irradiation stop with X-rays or the irradiation stop signal is exchanged through the dedicated I/F, the signal transmission control is not performed by the electronic cassette side, which is simple.

The X-ray generator and the X-ray imaging apparatus made of different markers are often used and do not know the detailed processes to be performed thereby. Accordingly, when the X-ray source and the source controller and the electronic cassette and the console made by different manufacturers are combined, it is difficult to guarantee that the process of stopping the irradiation with X-rays is performed without hindrance. In this embodiment, since the detection signal associated with the determination of the irradiation stop with X-rays or the irradiation stop signal is exchanged through the dedicated I/F, the operation of a system into which they are combined is guaranteed, which is preferable, by evaluating the transmission performance of a signal of the electronic cassette side and the reception performance of a signal of the source controller side and guaranteeing that the process of stopping the irradiation with X-rays is performed without hindrance.

The complication of the above-mentioned control slightly exists, but in consideration of the purpose of the speed-up of the process of stopping the irradiation with X-rays, only a signal which does not interfere in timing with the irradiation stop signal in the processing sequence of the system may be exchanged through the use of the dedicated I/F exchanging the irradiation stop signal without exchanging only the irradiation stop signal through the use of the dedicated I/F. In this case, the speed-up of the process of stopping the irradiation with X-rays is not affected in practice. Specifically, since it cannot be first thought that the irradiation start signal is generated at the time of stopping the irradiation with X-rays, the irradiation start signal is exchanged through the same I/F, and a signal such as a check signal of the remaining capacity of a battery which can be generated at any time (of which the timing is not periodic) is exchanged through the use of other I/F. This case excludes the case where the irradiation stop is determined using the detection signal, and is limited to the case where the irradiation stop is determined using the irradiation stop signal.

In the examples shown in FIGS. 19 and 20, the irradiation signal I/F 27 of the source controller 11 and the irradiation signal I/F 81 of the electronic cassette 13 may exchange a signal other than the detection signal or the irradiation stop signal in a wireless manner, in addition to the wireless communication with the console 14. By surely transmitting and receiving the detection signal or the irradiation stop signal in a wired manner and transmitting and receiving other signals in a wireless manner, the mobility of the electronic cassette 13 is guaranteed.

Guarantee of Safety

When a problem is caused in the detection pixels 65 of the electronic cassette 13 or the communication between the source controller 11 and the electronic cassette 13 is broken during radiography due to wiring disconnection or the like, it may be considered that the detection signal or the irradiation stop signal is not correctly transmitted and received and the AEC does not work. Particularly, the maximum value of the tube current-irradiation time product is set as the radiographing conditions in the source controller 11 side. Accordingly, when the AEC does not work, the radioactivity exposure of a patient may be higher than the upper limit. Therefore, a test mode is provided to the electronic cassette 13 and a test radiographing is performed with all the radiographing conditions of the console 14 just after the installation or before the radiography of the day. When the electronic cassette 13 continuously detects X-rays with the detection pixels 65 after transmitting the irradiation stop signal or the detection signal corresponding to the irradiation stop signal to the source controller 11 and the irradiation stop with X-rays is detected within a predetermined time, it is determined that the AEC is performed normally. When the irradiation stop with X-rays is not detected, it is determined that a certain disorder is present, and a warning message is displayed on the display 89 of the console 14.

By configuring the detection signal I/F 26 and 80 or the irradiation signal I/F 27 and 81 of the source controller 11 and the electronic cassette 13 to be connected to each other in both the wired manner and the wireless manner, an alarm may be displayed to switch the wired manner when it is determined as the monitoring result of radio field intensity or the like that the wireless communication is not stable.

In the above-mentioned embodiment, the example where the numbers of the X-ray source 10, the electronic cassette 13, and the console 14 are only one and are connected to each other in a one-to-one manner is described above for the purpose of convenient explanation. However, in the present invention, it is assumed that a pair of an X-ray source and a console is disposed for each radiography room or each round visiting car and several electronic cassettes are shared by the radiography rooms or the round visiting cars or the operations of the X-ray sources of plural platforms are collectively managed by a single console, for example, when a group medical examination is carried out in a relatively large-scale hospital or in round visiting cars. In the former, the individual configurations are the same as in the one-to-one connection in the above-mentioned embodiment, and thus the source ID is transmitted and received when the communication between the X-ray source and the console is set up, as in the above-mentioned embodiment. In the latter, the X-ray source among the X-ray sources of plural platforms should be used for the radiography can be made to be selected on the GUI of the display of the console and the source ID of the selected X-ray source is exchanged between the X-ray source and the console.

In the above-mentioned embodiment, the source information 99 is stored in the storage device 87 of the console 14 and the regional type or the correction information is transmitted from the console 14 to the electronic cassette 13, but the present invention is not limited to this configuration. For example, the source information 99 may be stored in a built-in memory (not shown) of the control unit 41 of the electronic cassette 13. In this case, the source ID is transmitted to the electronic cassette via the console. When the X-rays sources are provided to correspond to plural platforms, the information of the correlation between the specific ID of the console or a wireless access point (when the console and the electronic cassette are connected to each other in a wireless manner) such as an IP address, an SSID, and an ESSID and the source ID may be stored in the electronic cassette, the ID may be acquired when accessing the console or the wireless access point, and the source ID corresponding to the acquired ID of the console or the wireless access point may be read from the information of the correlation. When the ID of a wireless access point is acquired, the wireless access point having the most excellent communication characteristics such as radio field intensity is selected. In the case of the round visiting cars, the IDs specific to the round visiting cars may be used instead of the IDs specific to the consoles or the wireless access points.

In the above-mentioned embodiment, the detection pixels 65 short-circuited to the signal lines 52 without passing through the TFTs 47 are used as the new AEC sensor. However, the current flowing in the bias line 48 connected to a specific pixel 45 may be monitored to detect the dose by using the fact that the current based on the charges generated in the pixel 45 flows in the bias line 48 supplying the bias voltage Vb to the respective pixels 45. The does may be detected on the basis of the charges leaking from the pixel 45 when all the TFTs 47 are turned off. An AEC detection pixel having a different configuration and having an independent output may be provided in the same plane as the imaging plane 36 independently of the pixels 45.

Instead of causing the integration circuit to integrate the detection signal after the correction circuit corrects the detection signal, the integrated value of the detection signal output from the integration circuit may be corrected. In this case, the new AEC detection signal is input to the integration circuit from the detection field selecting circuit, the integration circuit integrates the new AEC detection signal, the resultant is input to the correction circuit, and the same correction as described in the above-mentioned embodiment is performed.

In the above-mentioned embodiment, a so-called retrofitting is described above in which the old AEC sensor 25 included in the X-ray source 10 is brought into disuse and the detection pixels 65 of the electronic cassette 13 are newly used as the AEC sensor. However, even when the X-ray source and the like are made by different manufacturers and only the electronic cassette is supplied as products of the corresponding manufacturer in an OEM manner, the output format of the automatic exposure control signal needs to be changed to suitable for the X-ray source and the like made by another manufacturer and thus the present invention can be applied thereto similarly.

In the above-mentioned embodiment, it is stated that the console 14 and the electronic cassette 13 are separated components. However, the console 14 does not need to be an independent apparatus, and the functions of the console 14 may be mounted on the electronic cassette 13. The present invention can be applied to an X-ray image detector which is fixed to a radiography platform, as well as the electronic cassette which is the portable X-ray image detector.

In the above-mentioned embodiment, the correction circuit 76 correcting the new AEC detection signal to a detection signal corresponding to the old AEC detection signal is provided for the reason of mismatch in AEC specification between the source controller and the electronic cassette, but the correction circuit 76 is not necessary when both match each other.

The present invention can be applied to a radiographic system using other radiation such as γ-rays other than X-rays.

What is claimed is:

1. A radiographic system having
a radiation source that irradiates an object with radiation,
a source controller that controls the radiation source, and
a radiological image detector that receives the radiation passing through the object to detect a radiological image and that has an AEC sensor performing an automatic exposure control of detecting the dose of the radiation passing through the object and stopping irradiation with the radiation from the radiation source when the integrated value of the detected dose reaches a predetermined irradiation-stop threshold,
the radiographic system implementing the automatic exposure control by exchanging any one of a detection signal of the AEC sensor and an irradiation stop signal based on a comparison result of the integrated value of the detection signal of the AEC sensor and the irradiation-stop threshold between the source controller and the radiological image detector,
the radiographic system comprising:
an information acquiring part for acquiring type information on an installation convenience preference type in which convenience in connection between the source controller and the radiological image detector is preferred or an installation convenience non-preference type; and
a switching part for selectively switching an output format of an automatic exposure control signal so as to exchange the detection signal between the source controller and the radiological image detector when the type acquired by the information acquiring part is the installation convenience preference type, and to exchange the irradiation stop signal between the source controller and the radiological image detector when the type acquired by the information acquiring part is the installation convenience non-preference type.

2. The radiographic system according to claim 1, further comprising a first storage part for storing source information in which a source ID specific to the radiation source and a type are correlated with each other,
wherein the information acquiring part acquires the type information by acquiring a source ID and retrieving and extracting the type correlated with the acquired source ID from the source information.

3. The radiographic system according to claim 2, wherein the source information includes a list of regions and the installation convenience preference type or the installation convenience non-preference type corresponding to each region.

4. The radiographic system according to claim 1, further comprising:
a display part for displaying a GUI receiving an input of the type; and
an input device to which the type is input through the use of the GUI,
wherein the information acquiring part acquires the type information from the input result of the type through the input device.

5. The radiographic system according to claim 1, wherein the radiological image detector has a detection signal I/F outputting the detection signal and an irradiation signal I/F outputting the irradiation stop signal, and
wherein the switching part is disposed in the radiological image detector, selects the detection signal I/F as the output destination of the automatic exposure control signal when the type acquired by the information acquiring part is the installation convenience preference type, and selects the irradiation signal I/F as the output destination of the automatic exposure control signal when the type acquired by the information acquiring part is the installation convenience non-preference type.

6. The radiographic system according to claim 1, further comprising a converter that is connected to both the source controller and the radiological image detector and that relays exchange of the signals,
wherein the switching part is disposed in the converter.

7. The radiographic system according to claim 6, wherein the radiological image detector has only a detection signal I/F outputting the detection signal,
wherein the converter has an irradiation signal I/F outputting the irradiation stop signal in addition to a detection signal I/F, and
wherein the switching part selects the detection signal I/F as the output destination of the automatic exposure control signal when the type acquired by the information acquiring part is the installation convenience preference type, and selects the irradiation signal I/F as the output destination of the automatic exposure control signal when the type acquired by the information acquiring part is the installation convenience non-preference type.

8. The radiographic system according to claim 1, wherein the information acquiring part acquires the type information when the AEC sensor attached to the radiological image detector is connected to the source controller for use instead of an old AEC sensor.

9. The radiographic system according to claim 8, wherein the information acquiring part acquires positional information of a detection field of the old AEC sensor,
wherein the radiographic system further comprises detection field selecting part for selecting a detection field of the AEC sensor so as to match the detection field of the old AEC sensor on the basis of the positional information of the detection field of the old AEC sensor, and
wherein the detection field selecting part selects the detection field depending on the posture of the radiological image detector.

10. The radiographic system according to claim 8, further comprising a correction part for correcting the detection signal of the AEC sensor to a detection signal corresponding to the detection signal of the old AEC sensor so as to exclude the influence on the detection signal due to a variation in constitution of an intermediate member which is disposed between the radiation source and an imaging plane of a detection panel of the radiological image detector when the AEC sensor is used instead of the old AEC sensor.

11. The radiographic system according to claim 10, further comprising a second storage part for storing a correlation between the detection signal of the AEC sensor and the detection signal of the old AEC sensor,
wherein the correction part performs the correction on the basis of the correlation between the detection signal of the AEC sensor and the detection signal of the old AEC sensor.

12. The radiographic system according to claim 10, wherein the intermediate member includes at least one of a housing covering the detection panel of the radiological image detector, a scintillator converting radiation into visible rays, and a grid removing radiation scattered in the object.

13. The radiographic system according to claim 10, further comprising an integration part for integrating the detection signal output from the correction part.

14. The radiographic system according to claim 13, wherein the information acquiring part acquires information on whether the source controller has a function of integrating the detection signal, and
wherein the switching part outputs the detection signal output from the correction part without passing through the integration part when the type acquired by the information acquiring part is the installation convenience preference type and the source controller has the function of integrating the detection signal, and outputs the integrated value of the detection signal output from the integration part when the source controller does not have the function of integrating the detection signal or not.

15. The radiographic system according to claim 13, wherein the information acquiring part acquires the irradiation-stop threshold set by the source controller, and
wherein the radiographic system further comprises a comparison part for comparing the integrated value of the detection signal output from the integration part with the irradiation-stop threshold set by the source controller and outputting the irradiation stop signal when the integrated value of the detection signal reaches the irradiation-stop threshold.

16. The radiographic system according to claim 15, further comprising
a converter that is connected to both the source controller and the radiological image detector and that relays exchange of the signals,
wherein the information acquiring part acquires positional information of a detection field of the old AEC sensor,
wherein the radiographic system further comprises a detection field selecting part for selecting a detection field of the AEC sensor so as to match the detection field of the old AEC sensor on the basis of the positional information of the detection field of the old AEC sensor, and
the detection field selecting part, the correction part, the integration part, and the comparison part are disposed in the radiological image detector or the converter.

17. The radiographic system according to claim 1, wherein an inquiry signal for inquiring whether the irradiation of radiation should be started and an irradiation permission signal permitting the irradiation of radiation are exchanged between the source controller and the radiological image detector, when the type acquired by the information acquiring part is the installation convenience non-preference type.

18. The radiographic system according to claim 1, wherein the AEC sensor attached to the radiological image detector is a pixel directly connected to a signal line for reading signal charges without using a switching element.

19. The radiographic system according to claim 1, wherein the radiological image detector is an electronic cassette in which a detection panel is received in a portable housing.

20. An automatic exposure control method of a radiographic system having
a radiation source that irradiates an object with radiation,
a source controller that controls the radiation source, and
a radiological image detector that receives the radiation passing through the object to detect a radiological image and that has an AEC sensor performing an automatic exposure control of detecting the dose of the radiation passing through the object and stopping irradiation with the radiation from the radiation source when the integrated value of the detected dose reaches a predetermined irradiation-stop threshold,
the radiographic system implementing the automatic exposure control by exchanging any one of a detection signal of the AEC sensor and an irradiation stop signal based on a comparison result of the integrated value of the detection signal of the AEC sensor and the irradiation-stop threshold between the source controller and the radiological image detector,
the automatic exposure control method comprising:
an information acquiring step of acquiring type information on an installation convenience preference type in which convenience in connection between the source controller and the radiological image detector is preferred or an installation convenience non-preference type; and
a switching step of selectively switching an output format of an automatic exposure control signal so as to exchange the detection signal between the source controller and the radiological image detector when the type acquired in the information acquiring step is the installation convenience preference type and to exchange the irradiation stop signal between the source controller and the radiological image detector when the type acquired by the information acquiring part is the installation convenience non-preference type.

21. A radiological image detector that receives radiation passing through an object to detect a radiological image, comprising:
an AEC sensor that performs an automatic exposure control of detecting the dose of the radiation passing through the object and stopping irradiation with the radiation from a radiation source when the integrated value of the detected dose reaches a predetermined irradiation-stop threshold,
wherein the automatic exposure control is implemented by exchanging any one of a detection signal of the AEC sensor and an irradiation stop signal based on a comparison result of the integrated value of the detection signal of the AEC sensor and the irradiation-stop threshold with a source controller controlling the radiation source, and
wherein an output format of an automatic exposure control signal is selectively switched so as to exchange the detection signal with the source controller and the radiological image detector in the case of an installation convenience preference type in which convenience in connection to the source controller is preferred and to exchange the irradiation stop signal with the source controller in the case of an installation convenience non-preference type.

* * * * *